(12) United States Patent
Xu

(10) Patent No.: US 7,919,123 B2
(45) Date of Patent: Apr. 5, 2011

(54) COMPOSITION AND METHOD FOR TREATING OR PREVENTING GASTROINTESTINAL CANCER

(76) Inventor: Rongxiang Xu, Arcadia, CA (US)

( * ) Notice: Subject to any disclaimer, the term of this patent is extended or adjusted under 35 U.S.C. 154(b) by 501 days.

(21) Appl. No.: 11/952,046

(22) Filed: Dec. 6, 2007

(65) Prior Publication Data

US 2008/0096854 A1 Apr. 24, 2008

Related U.S. Application Data

(60) Division of application No. 11/687,512, filed on Mar. 16, 2007, now Pat. No. 7,399,492, which is a division of application No. 11/276,845, filed on Mar. 16, 2006, now Pat. No. 7,211,276, which is a continuation of application No. 10/669,094, filed on Sep. 22, 2003, now Pat. No. 7,074,438, which is a division of application No. 10/004,103, filed on Oct. 30, 2001, now Pat. No. 6,685,971.

(60) Provisional application No. 60/301,961, filed on Jun. 28, 2001.

(51) Int. Cl.
A61K 36/00 (2006.01)
A61K 35/00 (2006.01)
A61K 35/56 (2006.01)

(52) U.S. Cl. ........ 424/725; 424/520; 424/400; 424/537; 424/539

(58) Field of Classification Search .................. 424/400, 424/461, 464, 476, 520, 637, 639, 725
See application file for complete search history.

(56) References Cited

U.S. PATENT DOCUMENTS

| | | | |
|---|---|---|---|
| 4,016,273 | A | 4/1977 | Sieger et al. |
| 4,382,886 | A | 5/1983 | Sosnowski |
| 5,372,943 | A | 12/1994 | Inlow et al. |
| 5,405,608 | A | 4/1995 | Xu |
| 5,466,443 | A | 11/1995 | Ho et al. |
| 5,486,510 | A | 1/1996 | Bouic et al. |
| 5,496,813 | A | 3/1996 | Eugster et al. |
| 5,531,991 | A | 7/1996 | Cheng et al. |
| 5,552,148 | A | 9/1996 | Znaiden et al. |
| 5,759,830 | A | 6/1998 | Vacanti et al. |
| 5,817,322 | A | 10/1998 | Xu |
| 5,853,755 | A | 12/1998 | Foldvari |
| 5,993,795 | A | 11/1999 | Osawa et al. |
| 6,306,435 | B1 | 10/2001 | Chen et al. |
| 6,365,198 | B1 | 4/2002 | Niazi |
| 6,685,971 | B2 | 2/2004 | Xu |
| 6,833,271 | B2 | 12/2004 | Bertheussen |
| 6,972,195 | B2 | 12/2005 | Xu |
| 6,991,813 | B2 | 1/2006 | Xu |
| 7,074,438 | B2 | 7/2006 | Xu |
| 7,211,276 | B2 | 5/2007 | Xu |
| 7,399,492 | B2 | 7/2008 | Xu |
| 2003/0021850 | A1 | 1/2003 | Xu |
| 2004/0063205 | A1 | 4/2004 | Xu |
| 2006/0051864 | A1 | 3/2006 | Xu |
| 2006/0153927 | A1 | 7/2006 | Xu |
| 2006/0292692 | A1 | 12/2006 | Xu |
| 2007/0166374 | A1 | 7/2007 | Xu |
| 2008/0085322 | A1 | 4/2008 | Xu |
| 2008/0089945 | A1 | 4/2008 | Xu |
| 2008/0131528 | A1 | 6/2008 | Xu |

FOREIGN PATENT DOCUMENTS

| | | |
|---|---|---|
| EP | 0211691 A2 | 2/1987 |
| EP | 0211691 A3 | 3/1987 |
| EP | 0763362 A2 | 3/1997 |
| EP | 0763362 A3 | 4/1998 |
| JP | 61050919 A | 3/1986 |
| JP | 07304684 | 11/1995 |
| JP | 09208598 | 8/1997 |

OTHER PUBLICATIONS

Awad, A.B., et al. Effect of Sterols on Prostate Cancer Growth and Metastasis in Vitro. FASEB Journal. (Mar. 7, 2001). vol. 15. No. 4: A599 (482.2).
Bhadra, S., et al. Incorporation of Liposomal Phytosterols Into Human Cells in Culture. Biochemical Medicine and Metabolic Biology. 1991. 46: 119-124.
Codex Standard for Named Vegetable Oils, CX-STAND 210-1999, Codex Alimentarius, vol. 8: 11-25, 2001.
Debridement, Dr. Joseph F. Smith Medical Library, http://www.chclibrary.org/micromed/00044870.html (accessed Mar. 6, 2005).
Garciamore, S. M. Diet food prepn. Derwent. 91-351349. Oct. 1991. XP-002052813. (Asbtract only).
Hoffman, P. C., et al. Effect of Oxygenated Sterol Compounds on Human Bone Marrow Granulocytic Progenitor Cells. Blood. (Jan. 1981) vol. 57. No. 1: 164-169.
Huang bai (chuan, huang bo). 2002. Available at http://botanicum.com/singles/huangbaichuan.htm. Accessed Oct. 31, 2002.
Huang Bai (Phellodendron chinense). 2001. Available at http://www.herbalists.on.ca/resources/freeman/PHELLODE.html. Accessed Oct. 31, 2002.
Huang Lian (Coptis chinensis). 2001. Available at http://www.herbalists.on.ca/resources/freeman/COPTIS.html. Accessed Oct. 31, 2002.
Huang Qin (Scutellaria baicalensis). 2001. Available at http://www.herbalists.on.ca/resources/freeman/SCUTELLA.html. Accessed Oct. 31, 2002.
Huang, Qin, DrugDigest. Available at http://www.drugdigest.org/DD/DVH/HerbsWho/0,3923,552023|Huang+Qin,00.html. Accessed Mar. 6, 2005.
Panaitescu, et al. Gasstric and duodenal ulcer treatment agent—comprises mint water belladonna syrup, carboxy methyl cellulose mucilage and preservative soln.blend. Derwent. 1990-373889. Apr. 30, 1990. (Abstract only).
Xu, R. X. Burns Regenerative Medicine and Therapy. Xia Sun, Editor. Basel, Switzerland: Karger Publishers; 2004.

Primary Examiner — Ruth A Davis
(74) Attorney, Agent, or Firm — Wilson Sonsini Goodrich & Rosati

(57) ABSTRACT

The present invention provides novel compositions and methods for repair and regeneration of tissues or organs of the body, especially mucosa in the gastrointestinal tract. The composition can be used as a pharmaceutical or nutraceutical to treat or prevent gastrointestinal cancer such as colorectal carcinoma, stomach cancer and esophagus cancer. The composition is in an oral dosage form and comprises edible oil homogenized with a sterol compound at a concentration of at least 0.5% by weight and edible wax at a concentration ranging from 3% to 30% by weight.

22 Claims, 10 Drawing Sheets

COMPOSITION AND METHOD FOR TREATING OR PREVENTING GASTROINTESTINAL CANCER

CROSS REFERENCE TO RELATED APPLICATIONS

This application is a divisional of U.S. application Ser. No. 11/687,512, filed Mar. 16, 2007, now U.S. Pat. No. 7,399,492 which is a divisional of U.S. application Ser. No. 11/276,845, filed Mar. 16, 2006, now U.S. Pat. No. 7,211,276, which is a continuation of U.S. application Ser. No. 10/669,094, filed Sep. 22, 2003, now U.S. Pat. No. 7,074,438, which is a divisional of U.S. patent application Ser. No. 10/004,103, filed Oct. 30, 2001, now U.S. Pat. No. 6,685,971, which claims priority to U.S. Provisional Application No. 60/301,961, filed Jun. 28, 2001, which applications are incorporated herein by reference in their entirety.

BACKGROUND OF THE INVENTION

1. Field of Invention

The present invention relates to methods and compositions for oral delivery of nutrients and/or pharmaceuticals, particularly for tissue repair and regeneration of the body, and more particularly to methods and compositions for protecting the mucosal tissue from damages caused by irritants and for promoting repair and regeneration of damaged or dysfunctional mucosal tissue in the gastrointestinal tract, especially for the treatment of gastrointestinal disorders such as gastritis, peptic ulcer, reflux esophagitis, dyspepsia, and gastric cancer, and the restoration of the physiological structure and function to the mucosal tissue.

2. Description of Related Art

Mucosal tissues (also termed mucosa) are membranes that line body cavities such mouth, nose, eyelids and sexual organs, and canals such as alimentary canals (e.g., the gastrointestinal (GI) tract) and the respiratory tract. Since mucosa is exposed to the external air, it secrets mucus to moisten and protect itself from adversary effects of environmental elements.

Mucosa is primarily comprised of epithelial cells that are attached to the basement membrane. Unlike the mucosal tissue of the inner surface of the eyelids, the epithelial cells which line the inside of the stomach are exposed to much harsher conditions, e.g., acid (i.e., hydrochloric acid), sometimes alcohol, enzymes (e.g., pepsin) for digesting food, and waste generated therefrom. Mucous secretion essentially protects the cells on the inside of the stomach and duodenum from damage by acid or enzymes, for example by presenting bicarbonate to neutralize some of the effects of acid on the stomach's inner lining, and inhibitors to block the enzymatic activity. Once the mucous secretions of the epithelial cells stop, the inner lining of the stomach or duodenum would eventually be eroded by the combined action of acid and enzymes, leading to ulcer.

Modern medical research has identified many factors attributable to the formation of various gastrointestinal diseases, such as acute gastritis, chronic superficial gastritis, atrophic gastritis, antral gastritis, senile gastritis, bile-regurgitational gastritis, esophagitis, gastroduodenal ulcer, indigestion, gastric neurosis, constipation, as well as various consequent conditions including gastric hyperacidity, hypochlorhydria, flatulency, gastrointestinal discomfort after meals, gastric discomfort after drinking, and gastric discomfort due to fasting. The factors include: (1) drinking, smoking, medication as well as other factors that destroy the barrier of gastric mucous membrane by directly damaging gastric mucous membrane or stimulating gastric acid secretion; (2) infection of all kinds of microorganism and their toxins causing the damage of gastrointestinal mucous membrane; (3) immunity factors: weakened immunologic function causing a decrease in the content of secretory IgA in gastrointestinal fluid that impairs the body discharging of bacteria and toxin, further damaging the gastrointestinal mucous membrane; (4) the regurgitation of duodenum which removes mucus on the surface of the gastric mucous membrane, thereby destroying the barrier of gastric mucous membrane; (5) chronic gastritis, leading to gastric ulcer; (6) constipation, which causes or contributes to gastrointestinal diseases; and (7) damage of intestinal wall nerves' structure due to intestinal diseases thereby resulting in constipation, etc.

The physiological mechanisms of mucosal injury in gastritis and peptic ulcer diseases are thought to be an imbalance of aggressive factors, such as acid production or pepsin, and defensive factors, such as mucus production, bicarbinate, and blood flow. Erosive gastritis usually is associated with serious illness or with various drugs. Stress, ethanol, bile, and nonsteroidal anti-inflammatory drugs disrupt the gastric mucosal barrier, making it vulnerable to normal gastric secretions. Infection with *Helicobacter pylori*, a short, spiral-shaped, microaerophilic gram-negative bacillus, is widely believed to be the leading cause of peptic ulcer diseases. *H. pylori* colonize the deep layers of the mucosal gel that coats the gastric mucosa and presumably disrupt its protective properties. *H. pylori* is thought to infect virtually all patients with chronic active gastritis.

Various medications have been developed to treat above described conditions associated with damaged or malfunctional mucosal tissues in the GI tract. One approach is to neutralize gastric acid by using antacids to relieve symptoms of gastritis. For example, aluminum and magnesium hydroxide (MAALUX® and MYLANTA®) neutralize gastric acidity, resulting in increase in pH in the stomach and duodenal bulb. Aluminum ions inhibit smooth muscle contraction, thus inhibiting gastric emptying. Aluminum and magnesium antacid mixtures are used to avoid bowel function changes.

Another approach is to use H2-receptor antagonists to inhibit the action of histamine on the parietal cell, which inhibits acid secretion. Examples of H2-receptor antagonists include cimetidine (TAGAMET®), nizatidine (AXID®), ranitidine hydrochloride (ZANTAC®) lansoprazole (PREVACID®), and rabeprazole (ACIPHEX®). Cimitidine inhibits histamine at H2 receptors of the gastric parietal cells, resulting in reduced gastric acid secretion, gastric volume, and reduced hydrogen concentrations. Nizatidine competitively inhibits histamine at H2 receptors of gastric parietal cells, also resulting reduced gastric acid secretion, gastric volume, and reduced hydrogen concentrations. Lansoprazole decreases gastric acid secretion by inhibiting the parietal cell $H^+/K^+$ ATP pump, and is to relieve symptoms of active duodenal ulcers and erosive esophagitis. Rabeprazole also decreases gastric acid secretion by inhibiting the parietal cell $H^+/K^+$ ATP pump, and is used for short-term treatment and symptomatic relief of gastritis, and for the treatment of active duodenal ulcers, and all grades of erosive esophagitis.

These anti-acids or anti-ulcer drugs, although capable of alleviating the symptoms temporarily, have not been shown to be very effective in complete curing of ulcer and in preventing recurrence. After the treatment, mucosa may be repaired but the physiological structure and function of the mucosa have not been restored. In addition, long-term usage of these drugs at high dosages could have various side effects such as constipation, diarrhea, nausea and vomiting, abdominal discomfort and pain, and other adverse reactions in central nervous, cardiovascular, and hepatic systems. Thus, there exits a need for developing innovative compositions and methods for preventing damages to mucosa and for treating the mucosa in the GI tract using strategies different from those in the existing art.

SUMMARY OF THE INVENTION

Compositions and methods are provided for repairing and promoting regeneration of mucosa in the GI tract in order to restore physiological structure and function to the damaged or dysfunctional mucosa, to enhance the body's ability to absorb nutrients, to achieve healthy and balanced metabolism, and ultimately to promote the general health of the whole body. It should be noted that the compositions may be adapted for use in the treatment of dysfunctional mucosa of other organs, such as nasal, lung, anal, vaginal, aural, eye, and oral mucosa, as well as for tissue repair and regeneration of other organs such as heart, liver, pancreas, kidney, and lung.

In one embodiment, a composition suitable for oral administration is provided for promoting mucosal cell growth in the GI tract. The composition is in an oral dosage form and comprises: an edible oil homogenized with an edible wax at a concentration ranging from 0.5% to 50% by weight and a sterol compound at a concentration of at least 0.1% by weight.

The concentration of the sterol compound preferably ranges from about 0.5% to 20% by weight, more preferably about 1% to 10% by weight, and most preferably about 2% to 6% by weight.

The concentration of the edible wax preferably ranges from about 3% to 30% by weight, more preferably about 5% to 20% by weight, and most preferably about 6% to 10% by weight.

The edible wax may be any natural or synthetic wax suitable for oral administration to a human. Examples of edible wax include, but are not limited to, beeswax, castorwax, glycowax, and carnaubawax. In a preferred embodiment, the edible wax is beeswax.

The edible oil may be any natural or synthetic oil suitable for oral administration to a human. Examples of natural oil include, but are not limited to corn oil, wheat germ oil, soy bean oil, rice bran oil, rapeseed oil, sesame oil, fish oil and other vegetable and animal oils. In a preferred embodiment, the edible oil is sesame oil.

The composition may further comprise propolis at a concentration ranging from about 0.1% to 30% by weight, more preferably from about 1% to 20% by weight, and most preferably from about 5% to 10% by weight.

The composition preferably contains minimum amount of water, more preferably containing less than 0.5% of water by weight, and most preferably containing less than 0.1% water by weight.

For oral administration, the inventive composition can be formulated readily by combining with pharmaceutically acceptable carriers that are well known in the art. Such carriers enable the compounds to be formulated as tablets, pills, dragees, capsules, emulsions, gels, syrups, slurries, suspensions and the like, for oral ingestion by a patient to be treated.

In a preferred embodiment, the inventive composition is contained in capsules. Capsules suitable for oral administration include push-fit capsules made of gelatin, as well as soft, sealed capsules made of gelatin and a plasticizer, such as glycerol or sorbitol. More preferably, the inventive composition is contained in soft capsules. The inventive composition may be dissolved or suspended in suitable liquids, such as fatty oils or liquid polyethylene glycols. In addition, stabilizers may be added.

In another embodiment, a composition suitable for oral administration as a pharmaceutical or nutraceutical is provided. The composition comprises: an active ingredient; and an edible oil homogenized with an edible wax at a concentration ranging from 3% to 30% by weight, wherein the edible wax forms microcrystals which are dispersed substantially uniformly in the edible oil at ambient temperature. The size of the microcrystal is preferably between 0.1-100 µm, more preferably 5-70 µm, and most preferably 10-50 µm in length. The form of the microcrystals may vary depending on the concentration and temperature. At ambient temperature, the microcrystal may adopt a single, needle-like crystal form and/or form a microcrystal complex by aggregating with each other.

The composition may further comprise a sterol compound at a concentration ranging from 0.1% to 20% by weight, more preferably about 1% to 10% by weight, and most preferably about 2% to 6% by weight.

The active ingredient may be any drug for treating diseases or to promote general health, such as drugs in the class of 1) gastrointestinal agents; 2) antibiotics; 3) antiviral agents; 4) antifungal agents 5) antineoplastic agents; 6) analgesics; 7) tranquilizers; 8) narcotic antagonists; 9) antidepressants; 10) antihistamines; 11) antimigraine; 12) cardiovascular drugs; 13) calcium channel blockers; 14) appetite suppressant; 15) contraceptive agents; 16) corticosteroids; 17) local anaesthetics; 18) diuretics; 19) antihypertensive agents; 20) steroids; 21) prostaglandins; 22) anti-inflammatory drugs; 23) antithrombotic agents; 24) cardiac glycosides; 25) antiparkinsonism; 26) chemical dependency drugs; 27) acidic drugs such as salicylates (e.g., aspirin); and 28) peptides.

According to any of the above embodiments, the sterol compound may be an animal sterol or a plant sterol (also called phytosterol). Examples of animal sterol include cholesterol and all natural or synthesized, isomeric forms and derivatives thereof. Preferably, the sterol compound is selected from the group consisting of stigmasterol, campesterol, β-sitosterol, chalinosterol, clionasterol, brassicasterol, α-spinasterol, dancosterol, desmosterol, poriferasterol, and all natural or synthesized, isomeric forms and derivatives thereof. More preferably, the sterol compound is a combination of stigmasterol, β-sitosterol, and campesterol, collectively referred to herein as "sitosterol".

It is to be understood that modifications to the sterol compound i.e. to include side chains also fall within the purview of this invention. It is also to be understood that this invention is not limited to any particular combination of sterols forming a composition.

According to any of the above embodiments, the inventive composition may further comprise baicalin, preferably at a concentration ranging from about 0.01 to 5% by weight, more preferably about 0.1 to 2% by weight, and most preferably about 0.1% to 1% by weight.

According to any of the above embodiments, the inventive composition may further comprise an extract of huangqin (*Radix Scutellariae*) in aqueous solution, organic solvent such as oil and alcohol, or in a combination of water and organic solvent. Preferably, the edible oil in the composition is an extract of huangqin in the amount of 1-50% by weight in the oil. Preferably, the root of huangqin is used and may be obtained from the plant selected from one or more members of the group of *Scutellaria viscidula* Bge, *Scutellaria amoena* C. H. Wright, *Scutellaria rehderiana* Diels, *Scutellaria ikon-*

*nikovii* Juz, *Scutellaria likiangensis* Diels and *Scutellaria hypericifolia* Levl of Labiatae Family.

According to any of the above embodiments, the inventive composition may further comprise obaculactone, preferably at a concentration ranging from about 0.01 to 5% by weight, more preferably about 0.1 to 2% by weight, and most preferably about 0.1% to 1% by weight.

According to any of the above embodiments, the inventive composition may further comprise an extract of dry huangbai (*Phellodendron amurense* Rupr), in aqueous solution, organic solvent such as oil and alcohol, or in a combination of water and organic solvent. Preferably, the edible oil in the composition is an extract of huangbai in the amount of 1-50% by weight in the oil. Preferably, the bark of huangbai is used and may be obtained from the plant selected from one or more members of the group of *Phellodendron chinense Schneid, Plellodendron chinense Scheid* var. *glabriusculum Schneid, Phellodendron chinense Schneid* var. *omeiense* Huang, *Phellodendron Schneid* var. *yunnanense* Huang and *Phellodendron chinense Schneid* var. *falcutum* Huang.

According to any of the above embodiments, the inventive composition may further comprise obabenine, preferably at a concentration ranging from about 0.001% to 2% by weight, more preferably about 0.002% to 0.5% by weight, and most preferably about 0.003% to 0.1% by weight.

According to any of the above embodiments, the inventive composition may further comprise an extract of huanglian (*coptis chinensis* Franch), in aqueous solution, organic solvent such as oil and alcohol, or in a combination of water and organic solvent. Preferably, the edible oil in the composition is an extract of huanglian in the amount of 1-50% by weight in the oil. Root of huanglian is preferably used. Huanglian may be selected from one or more members of the group of *Coptis deltoidea* C. Y. Cheng et Hsiao, *Coptis omeiensis* (Chen) C. Y. Cheng, and *Coptis teetoides* C. Y. Cheng of Ranunculaceae Family.

According to any of the above embodiments, the inventive composition may further comprise berberine, preferably at a concentration ranging from about 0.001% to 2% by weight, more preferably about 0.002% to 0.5% by weight, and most preferably about 0.003% to 0.1% by weight.

According to any of the above embodiments, the inventive composition may further comprise narcotoline, preferably at a concentration ranging from about 0.001% to 2% by weight, more preferably about 0.002% to 0.5% by weight, and most preferably about 0.003% to 0.1% by weight.

According to any of the above embodiments, the inventive composition may further comprise an extract of puppy capsule (*Papaver somniferum* L.), in aqueous solution, organic solvent such as oil and alcohol, or in a combination of water and organic solvent. Preferably, the edible oil in the composition is an extract of puppy capsule in the amount of 1-20% by weight in the oil.

According to any of the above embodiments, the inventive composition may further comprise an extract of huangqin, huangbai and huanglian in aqueous solution, organic solvent such as oil and alcohol, or in a combination of water and organic solvent. Preferably, the edible oil in the composition is an extract of a combination of huangqin, huangbai and huanglian, the total amount of the combination being 1-50% by weight in the oil.

According to any of the above embodiments, the inventive composition may further comprise an extract of huangqin, huangbai, huanglian, and poppy capsule in aqueous solution, organic solvent such as oil and alcohol, or in a combination of water and organic solvent. Preferably, the edible oil in the composition is an extract of a combination of huangqin, huangbai, huanglian and poppy capsule, the total amount of the combination being 1-50% by weight in the oil.

According to any of the above embodiments, the inventive composition may further comprise various amino acids, preferably all 18 natural amino acids, for providing nutrition support to cell growth. The amino acids may be chemically synthesized or obtained from natural sources.

According to any of the above embodiments, the inventive composition may further comprise an extract of earthworms in aqueous solution, organic solvent such as oil and alcohol, or in a combination of water and organic solvent. Preferably, the edible oil in the composition is an extract of earthworms that is in the amount of 1-50% by weight in the oil.

According to any of the above embodiments, the inventive composition may further comprise an extract of huangqin, huangbai, huanglian, poppy capsule, and earthworms in aqueous solution, organic solvent such as oil and alcohol, or in a combination of water and organic solvent. Preferably, the edible oil in the composition is an extract of a combination of huangqin, huangbai, huanglian, poppy capsule, and earthworms, the total amount of the combination being 1-50% by weight in the oil.

In another aspect, the present invention provides methods for protecting and repairing mucosa, presumably by promoting the growth of regenerative mucosal cells. By using these methods, physiological structure and function of the damaged or dysfunctional mucosa may be restored to enhance the body's ability to absorb nutrients, which, in turn, can improve the body's general health and strength the immune system to fight diseases.

In an embodiment, a method is provided for preventing ulceration or irritation of mucosa in the gastrointestinal tract of a host. The method comprises: The method comprises: orally administering to the host a composition comprising an edible oil homogenized with an edible wax at a concentration ranging from 0.5% to 50% by weight and a sterol compound at a concentration of at least 0.1% by weight.

According to this embodiment, the host is preferably a human. As a prophylaxis, the composition may be administered to the host prior to consumption of alcohol, spicy food or other irritants to the stomach. Alternatively, the composition may be administered to the host post consumption of these irritants to the stomach.

In yet another embodiment, a method of treating a host having a gastrointestinal disorder. The method comprises: orally administering to a host having a gastrointestinal disorder a composition comprising an edible oil homogenized with an edible wax at a concentration ranging from 0.5% to 50% by weight and a sterol compound at a concentration of at least 0.1% by weight.

According to this embodiment, the host is preferably a human. The composition may be used as a pharmaceutical, a nutraceutical or a health food with or without a physician's prescription. The dosing regimen may vary depending on the severity of the condition of the host. The composition is preferably administered in an amount of 0.5-10 g per day, more preferably 2-8 g per day, and most preferably 3-6 g per day. For example, if the composition is supplied as 0.5 g soft gel capsules, 1-10 capsules may be administered twice a day.

Examples of the gastrointestinal disorder include, but are not limited to, gastrointestinal diseases, such as acute gastritis, chronic superficial gastritis, atrophic gastritis, antral gastritis, senile gastritis, bile-regurgitational gastritis, esophagitis, gastroduodenal ulcer, indigestion, gastric neurosis, constipation, as well as various consequent conditions including gastric hyperacidity, hypochlorhydria, flatulency, gastrointestinal discomfort after meals, gastric discomfort after drinking, and gastric discomfort due to fasting.

In yet another embodiment, a method is provided for treating a patient having a gastrointestinal cancer. The method comprises: orally administering to a patient having a gastrointestinal cancer a composition comprising an edible oil homogenized with an edible wax at a concentration ranging from 0.5% to 50% by weight and a sterol compound at a concentration of at least 0.1% by weight.

The gastrointestinal (GI) cancer can be an upper or lower GI cancer. Examples of the upper GI cancer include, but are not limited to, 1) esophagus cancer; 2) stomach cancer; 3) pancreas cancer; 4) liver cancer; and 5) cancer of bile ducts. Examples of the lower GI cancer include, but are not limited to, cancers of the large bowel such as colorectal carcinoma, primary lymphomas, melanoma, and sarcoma of the large bowel.

Also optionally, the inventive composition may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the inventive compositions for a few weeks up to over 100 days.

In yet another embodiment, a method is provided for manufacturing a composition for delivering active ingredients to a mucosal tissue in vivo. The method comprises: heating an edible wax at a temperature above its melting point; heating an edible oil at a temperature above the melting point of the edible wax; mixing the melted wax with the oil at a weight ratio ranging from 3:97 to 20:80; and homogenizing the mixture of the wax and oil.

According to this embodiment, the method may further comprise: adding the root of *Radix Scutellaria* to the edible oil at a weight ratio ranging from 1:99 to 10:90 and heating the mixture at a temperature above the melting point of the edible wax.

According to this embodiment, the method may further comprise: adding the homogenized mixture of the wax and oil into a gel capsule. The gel capsule may be a hard or a soft gel capsule.

The edible wax is preferably beeswax with a melting point of 70-80° C. and the edible oil is sesame oil.

The mixture of the wax and oil may be homogenized on a homogenizer, preferably at a speed of 6000-10000 rpm at 35-45° C. for 15-20 min. Alternatively, The mixture of the wax and oil may be homogenized on a colloid mill.

In yet another embodiment, a method is provided for manufacturing a composition for protecting or treating damaged mocosal tissue in vivo. The method comprises: heating a mixture of sesame oil and huangqin at a weight ratio between 70:30 and 98:2 at a temperature between 80-180° C. for 10-120 min; filtering the mixture to obtain a sesame oil filtrate; cooling the sesame oil filtrate to between 70-90° C.; adding beeswax to the sesame oil filtrate at a weight ratio between 3:93-10:90; heating the mixture of beeswax and the sesame oil filtrate with stirring at a temperature between 80-180° C. for 10-60 min; and homogenizing the mixture of beeswax and the sesame oil filtrate.

In yet another embodiment, a method is provided for manufacturing a composition for protecting or treating damaged mocosal tissue in vivo. The method comprises: heating a mixture of sesame oil and a combination of dry huangqin, huangbai, huanglian, poppy capsule and earthworm at a temperature between 80-180° C. for 10-120 min, the weight ratio between the sesame oil and the combination being between 70:30 and 98:2; filtering the mixture to obtain a sesame oil filtrate; cooling the sesame oil filtrate to between 70-90° C.; adding beeswax to the sesame oil filtrate at a weight ratio between 3:93-10:90; heating the mixture of beeswax and the sesame oil filtrate with stirring at a temperature between 80-180° C. for 10-60 min; and homogenizing the mixture of the mixture of beeswax and the sesame oil filtrate.

According to any of the above the method for manufacturing the composition, homogenizing the mixture of beeswax and the sesame oil filtrate may include homogenizing the mixture until particles or microcrystals of beeswax are substantially uniformly dispersed in the oil at ambient temperature.

DETAILED DESCRIPTION OF THE INVENTION

The present invention provides innovative methods and compositions for physiological repair and functional regeneration of mucosal tissues of the body, in particular, mucosa in the gastrointestinal (GI) tract. The groundbreaking innovation is multi-facet in both the conceptual and practical aspects, with a primary focus on the techniques for tissue repair and organ regeneration through induction and propagation of regenerative stem cells in situ and in vivo.

Figure 3A:
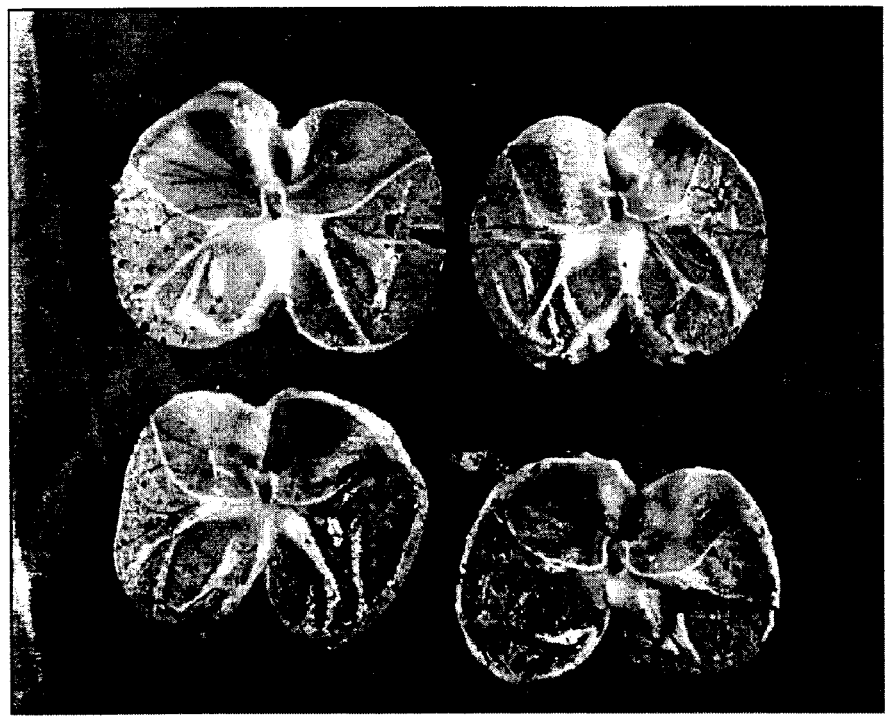
FIG. 3A shows the stomach of a rat suffered from severe ulcer after ingesting anhydrous alcohol.
Figure 3B:
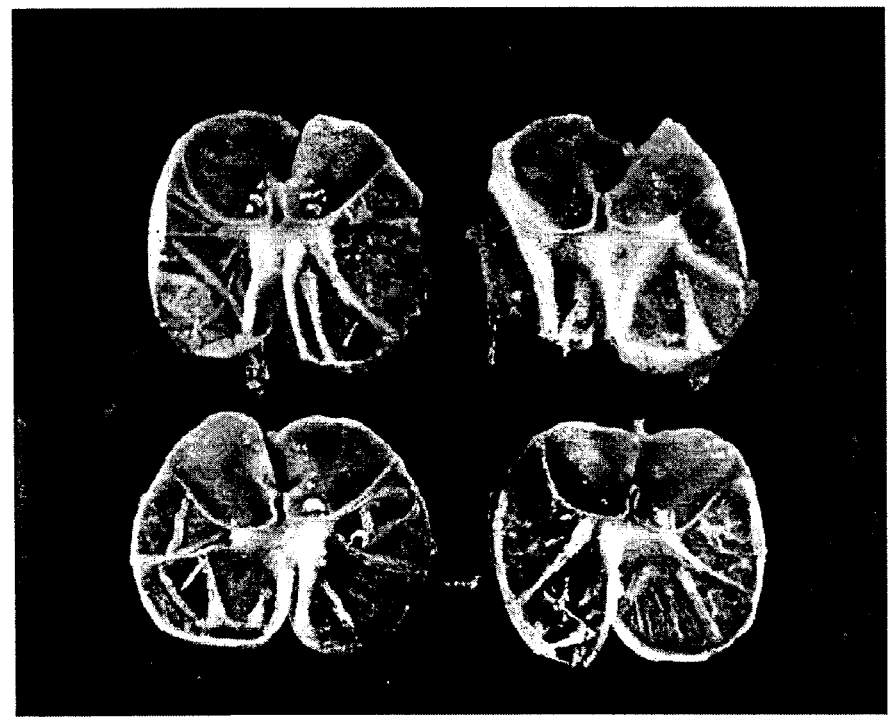
FIG. 3B shows the stomach of a rat that suffered from severe ulcer after ingesting anhydrous alcohol and was treated with the content of GI Capsules daily at 0.8 g/Kg for 3 weeks.

As shown in the EXAMPLE section, the inventor demonstrated experimentally that the inventive composition was able to sustain and stimulate strong growth of mucosal cells in vitro and to promote physiological healing of gastric ulcer in animal models. The inventor believes that the inventive composition can effectively repair the damaged mucosa by providing regenerative conditions in the GI tract, especially in the stomach. Upon administration to the GI tract, the inventive composition is mixed with mucus of the stomach and adheres to the mucosa to form a protective membrane. Such an artificial membrane protects the mucosa from further irritation of acid, alcohol, food and other material contained in the stomach. Under these conditions active ingredients in the composition are slowly released to the site to activate the regenerative stem cells there to promote fast repair of the mucosa. Since the inventive composition provides a condition favorable for regeneration in situ and in vivo, the mucosa can be repaired and/or regenerated with a restoration of its physiological structure and function. As shown in FIG. 3B, the inventive composition successfully cured gastric ulcer in animal models whereas the rats in the control group without the treatment still suffer severe gastric ulcer (FIG. 3A). Further, owing to its unique dosage form the inventive composition may also effectively inhibit the toxicity of the bacteria H. pylori by changing its morphology. With the regeneration of a healthy GI tract, the ulcerous conditions that are favorable for the habitation of H. pylori are destroyed, thereby indirectly inhibiting the growth of the bacteria. In addition, with the restoration of normal physiological structure and function to the damaged or dysfunctional mucosa, the body's ability to absorb nutrients is enhanced, which, in turn, leads to a healthy and balanced metabolism and general health of the whole body.

Departing from the traditional approaches for treating disorders in the GI tract by neutralizing acid or by inhibiting histamine H2-receptor with a single agent (e.g., ranitidine), the present invention discloses a completely different approach under the guidance of the following fundamental principle.

1. The Fundamental Principle of Adult Tissue Repair and Organ Regeneration

Figure 1:
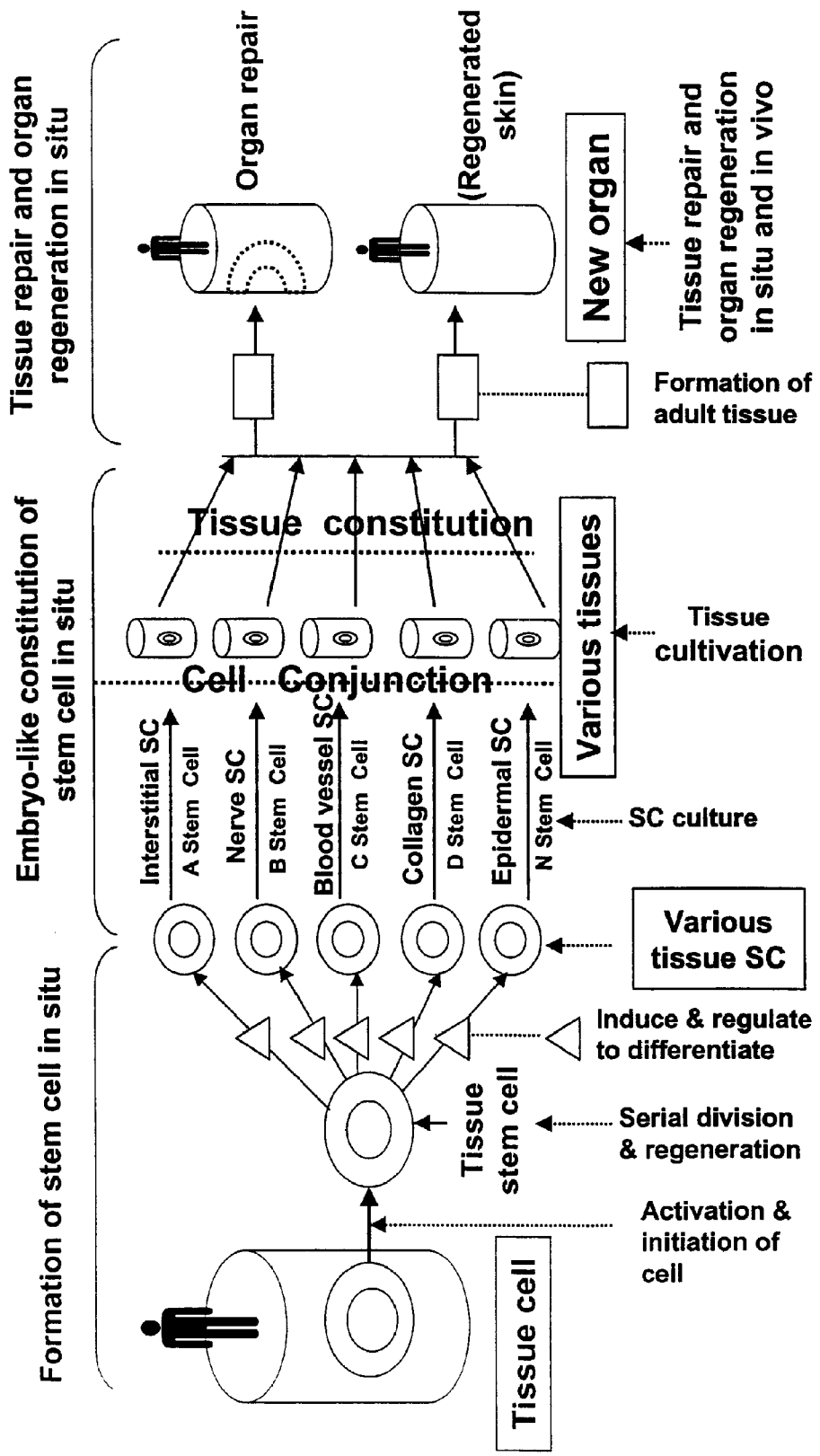
FIG. 1 illustrates the fundamental principle of adult tissue repair and organ regeneration according to the present invention.

The present invention reveals the fundamental principle of adult tissue repair and regeneration in vivo and in situ, which is illustrated in FIG. 1.

1) The Principle in General

In general, an adult, fully developed body has the ability to repair its damaged tissue and regenerate its organ in situ if the regenerative environment is provided. As illustrated in FIG. 1, in response to wound or other kinds of injury residual viable cells in the damaged organ can be activated and convert themselves into adult stem cells (ASCs), the counterpart of which are embryonic stem cells. Such induction of adult stem cells makes it possible that a large amount and a wide variety of cells needed for organ regeneration may be provided by these stem cells.

However, these nascent stem cells are quite fragile and are prone to death caused by cytotoxic effects exerted by various environmental elements, and by uncontrolled cellular responses to injury. As illustrated in FIG. 1, under suitable culturing conditions provided by the inventive compositions these adult stem cells proliferate and develop into various multipotent tissue stem cells by following the directions which are already genetically programmed at the embryonic development stages. Generation of such a multiple functional tissue stem cell assures ample supply of various types of cells that are needed for forming a physiologically functional tissue.

Still referring to FIG. 1, under optimum culturing conditions provided by the inventive compositions these tissue stem cells proliferate and differentiate into specific types of cells for particular kinds of tissues. Specific types of differentiated cells associate with each other through tissue-specific cell adhesion and form a nascent tissue. Such a mode of tissue-specific cell association is collectively referred to herein as "cell conjunction". The newly regenerated tissues then assemble into a nascent organ by forming organ-specific tissue-tissue junctions, mimicking the tissue assembly process in a developing fetus. Such a mode of organ specific tissue association in an adult is collectively referred to herein as "tissue constitution".

Finally, the nascent tissues within the reconstituted organ develop and mature into individual, functional tissues with physiologically balanced cell types and numbers under the regulation of the inventive composition. Meanwhile, these tissues undergo further remodeling through communications of tissues within the network of the live organ and eventually form a fully functional, mature organ (FIG. 1).

By following the above-described regenerative pathways, damaged or lost tissues can be repaired to regain their physiological structure and function. As demonstrated in the EXAMPLE section using rats as a model, ulcerous gastric tissue could be repaired with the inventive methodology.

The inventor believes that by in situ cultivation of regenerative stem cells within a live body under an optimum developmental condition, the damaged organ can be regenerated with a complete restoration of its physiological structures and functions. This regeneration process takes place spontaneously within the body under the regulation of both endogenous and exogenous materials provided in the present invention. Ultimately, successful organ regeneration depends on physiologically proper tissue-specific multi-cell adhesion, organic-specific multi-tissue assembly, and homeostatically balanced and immunologically compatible coexistence of multi-organs within a live body.

2) Redefinition of "Stem Cells"

Based on this fundamental principle and its successful application in organ regeneration in the clinic, the meaning of a stem cell is redefined in the present invention.

A classic definition of a stem cell is that a stem cell should have the following properties: 1) It is not itself terminally differentiated, i.e., not at the end of a pathway of diffentiation; 2) It can divide without limit or at least for the life time of the animal; and 3) When it divides, each daughter cell can either remain a stem cell, or embark on a course leading irreversibly to terminal differentiation. In Molecular Biology of the Cell, Alberts et al., eds, $3^{rd}$ ed. (1994), pp. 1155-1156, Garland Publishing Inc., New York and London.

According to this definition, stem cells isolated from human tissue, such as the embryonic stem cells isolated from the inner cell mass of human blastocysts, are still stem cells even if they are completely isolated from a live human body and reside in culture medium in vitro. These so-called stem cells, although capable of divide without limit and differentiate into cells of various tissue types, have not been shown to be able to regenerate a fully functional human organ, not even mentioning a live human in vitro.

To avoid confusion with the stem cells termed under the classic definition, the stem cell according to the present invention is termed as a "regenerative stem cell". This regenerative cell has the following characteristics: 1) it resides in a live body; 2) it is under the physiological control and regulation of the body; 3) it co-exists with the tissues and organs of the body, 4) it is capable of continuous cell division within the live body; 5) it is capable of repairing tissues, regenerating organs, and restoring physiological structures and functions to the regenerated organs.

3) Spontaneous Regeneration in the Body

The human body has considerable capacity for regeneration. Tissues with high rates of cell turnover, such as blood and epithelia, are regenerated continually through out life. Other Tissues, such as liver, bone, muscle, blood vessels, and adrenal cortex regenerate in response to injure. The liver regenerates by compensatory hyperplasia, whereas other tissues regenerate by the activation of reserve stem or progenitor cells perhaps by augmenting the regeneration of mesenchymally-derived tissues, or within the regenerating tissue. For example, hematopoietic cells such as T cells, B cells, neurotrophil, and erythrocytes are regenerated from hematopoietic stem cells in the bone marrow. Finger tips will regenerate if amputated distal to the terminal phalangeal joint. However, neither bone nor muscle will regenerate across a gap, and other organs as skin, pancreas, heart, and spinal cord respond to injury by the formation of scar tissue.

The distinct, novel approach disclosed in the present invention focuses on harnessing the body's inherent ability to repair and regenerate itself. Under optimum physiological conditions, such as bathing in the warm, sterile amniotic fluid, a fetus could heal its wound spontaneously without scar and loss of function. Unfortunately, a fully developed human is exposed to a completely different, more hostile environment. Under the influence of both endogenous and exogenous conditions, spontaneous adult wound healing and organ generation go through somewhat different pathways and end up with scars and dysfunction of organs. This spontaneous healing process is totally passive, uncontrolled by therapeutic interventions by embarking on a course of chaotic cell proliferation and differentiation and reconstitution of regenerated tissues. In addition, mucosa of the GI system, which is constantly exposed to harsh, acidic environment, once damaged, may not be able to repair itself without therapeutic intervention.

4) Methodology Developed in Application of the Principle

The present invention provides methods and compositions to actively control the whole process of tissue repair and organ regeneration. During this process, cells, the smallest unit of life, are stimulated, propagate, differentiate, integrate with each other to physiologically repair the damaged tissues or to regenerate the tissue destroyed in various courses, such as trauma and diseases. These nascent tissues then conjoin together to form a fully functional organ.

To achieve this result in an adult, specific, active human intervention is needed. The general guidance for this intervention revealed in the present invention is that 1) for injured or damaged tissues, the viable cells in the remaining tissues should be preserved to a maximum extent; 2) necrotic cells or tissues should be removed as early as possible; 3) the regenerative cells should be activated and propagated in an environment mimicking the their own native physiological conditions; and 4) regulators for cell growth and differentiation are administered to the regenerating organ to direct proper, physiological repair of tissues.

Figure 2:
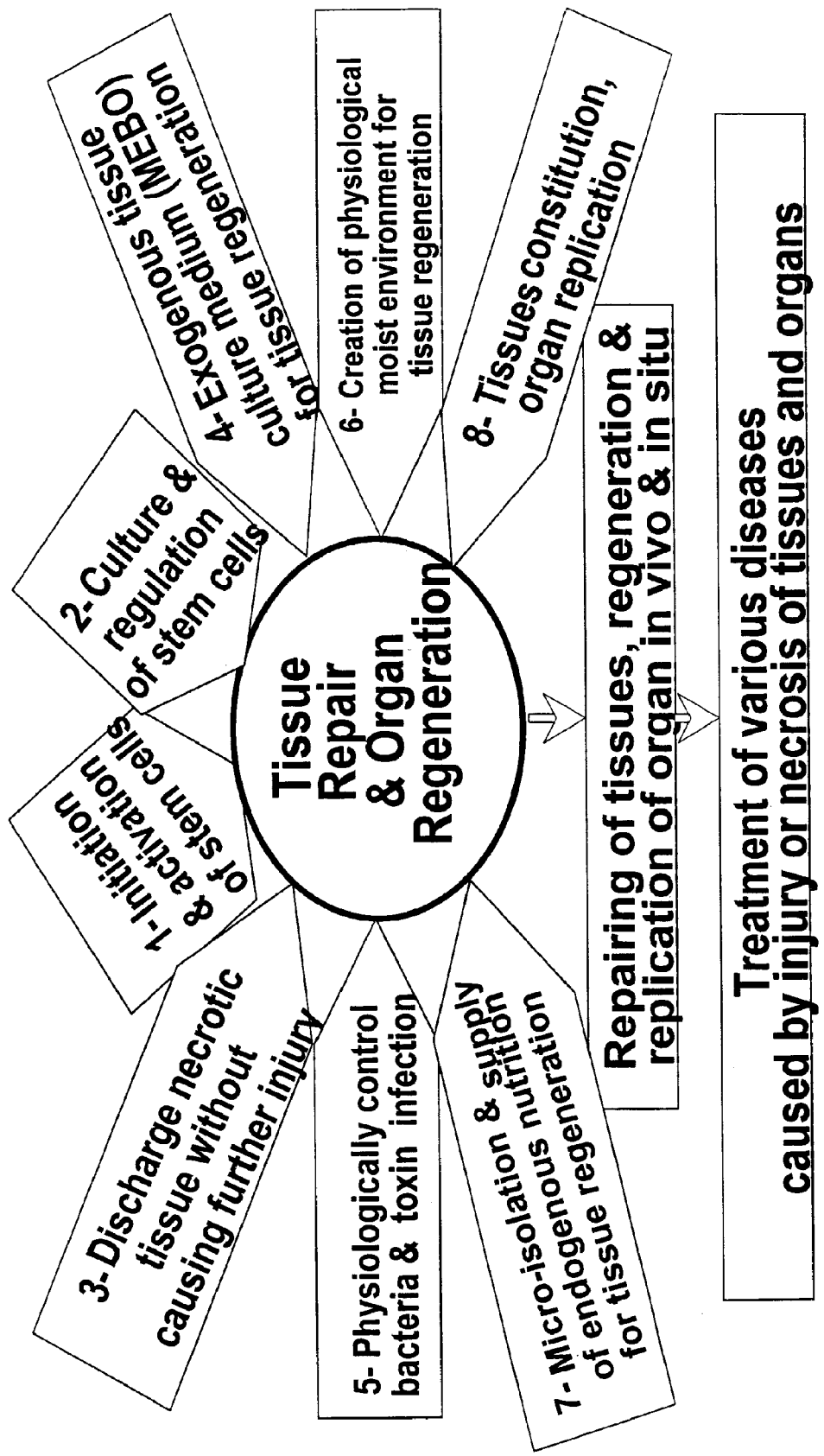
FIG. 2 depicts specific techniques used for cultivating adult regenerative stem cells and for promoting physiological tissue repair and functional organ regeneration.

Specifically, the methodology of the present invention covers the following eight techniques as illustrated by a block diagram in FIG. 2:

a) Activation and Regulation of Adult Stem Cells (ASCs)

Multipotent adult stem cells are produced in vivo and in situ by a) activating dormant tissue stem cells such as epithelial stem cells putatively residing in the bulge of a hair follicle, and or b) inducing dedifferentiation of fully dedifferentiated cells and converting them into ASCs.

b) Culture of ASCs In Vivo and In Situ

The fragile, nascent ASCs are cultured in a physiologically moist environment to allow rapid growth and directionally differentiation;

c) Discharge or Exudation of Liquefied Necrotic Tissues

Necrotic tissues of the mucosa are removed by adhering to the inventive composition and exudate from the wound automatically, thus greatly reducing the risk of physical or chemical injury to residual viable tissue;

d) Tissue Culturing In Vivo and In Situ in an Exogenous Culture Medium

ASCs and their differentiated cells are cultured in an exogenous culture medium provided by the present invention to allow rapid cell growth, integration and migration to physiologically repair the damaged tissue or regenerate lost tissue;

e) Inhibition of Toxicity of Bacteria by a Non-Bactericidal Mode of Action

Toxicity of bacteria infecting the wound are inhibited not by topically applying antibiotics to kill the bacterial cells, rather by allowing a bacterial cell to replicate genetically and change its morphology under a condition provided by an inventive composition, leading to reduced production of toxin; and thus greatly reduce inflammation caused by the body's immune response to bacterial toxin.

f) Creation of Physiologically Moist and Neutral Environment for Mucosa Regeneration By adhering to the mucosa in the stomach, for example, the inventive composition provides a moist and yet less acidic environment favorable for the growth of regenerative epithelial stem cells for the repair of ulcerous mucosa.

g) Micro-Isolation of Wound from Exterior Environment

Oral administration of an inventive composition to the GI tract results in formation of an artificial membrane by adhering to the mucosa. This membrane isolates the damaged mucosa from the exterior harsh environment and yet allows slow, sustained release of active ingredient and nutrients to the tissues beneath. As a result, mucosa and its underlying tissues can be regenerated, which, in turn, leads to restoration of normal functions of the organs in the GI tract, such as nutrient uptake and metabolism.

h) Supply of Oxygen and Nutrition Required for Regeneration

Various nutrients such as a full spectrum of natural amino acids, polysaccharides, fatty acids and phosphates are supplied exogenously. Oxygen required for cell growth can permeate through this membrane to reach the tissues beneath. Meanwhile, bacteria and other environmental contaminates are separated from the tissues undergoing repair and regeneration.

5) Comparison of the Present Methodology with Other Approaches in the Art

Clinical approaches current available to replace failing organs and tissues are organ transplantation and implantation of bionic device. The major drawbacks to organ transplantation are donor shortages and immunosuppressive side effects. The drawback to the approach of implantation of bionic device is the inability to manufacture artificial materials that duplicate the durability, strength, form, function, and biocompatibility of natural tissues.

At the experimental stage, regenerative medicine emerged in the last decade of the $20^{th}$ century has been focussed on implementation of two major strategies: transplantation of cells to form a new tissue in the transplant site and implantation of bioartificial tissues constructed in vitro.

Transplantation of cells involves ex vivo culturing and propagation of stem cells and then transplant them or their differentiated products to the site where the damaged organ resides. Although progress in biology has made it possible for apply the cell transplantation in the clinic, multiple practical limitations still exist and the clinical results are not physiological or cosmetically satisfactory. One of the limitations associated with this approach is the difficulties with identification and isolation of multipotent stem cells from various tissues. Although pluripotent human embryonic stem cell (ESC) lines have been cultured recently, directional differentiation of the ESCs remains a mystery.

Results obtained from experimental animals, although encouraging, still cannot translate functionally into human therapy confidently. For example, mouse neuronal and glial cells derived from neural stem cells in vitro, and cardiomyocytes derived from ESCs in vitro, integrate into the surrounding tissue when injected into an adult brain and heart, respectively. Multipotent human neural stem cells injected into the developing brain of mouse embryos migrate throughout the brain and differentiate site-specifically.

For successful organ regeneration using stem cells cultured in vitro, major obstacles lies in its way. Stem cells cultured in vitro must be directed to differentiate into site-specific phenotypes once they are transplanted into the lesion site. Complete deciphering of the signal needed for this process is required to guide the design of the in vitro tissue culturing conditions. Experimental data obtained by others in the art show that although multipotent human mesenchymal, mouse neural stem cells, and mouse embryonic stem cells can be grown in vitro through the addition of leukemia inhibitory factor (LIF) to the culture medium, mouse ESCs differentiate randomly in vitro and in vivo. Progress in the art has made it possible to induce differentiation of mouse ESCs into multipotent glial cell precursors in vitro and to transplant them into the brain of myelin-deficient fetal rats. However, question remains unanswered as to whether these multipotent stem cells harvested from specific tissues or differentiated from ESCs in vitro will make site-specific tissue when transplanted to injured adult tissues.

Immuno-rejection of the transplant is another major problem associated with cell transplantation. While autogeneic cells can be used in some instances (e.g., mesenchymal stem cells from bone marrow), most transplanted cells will be allogeneic. Attempts have been made to use genetic modification and cell biological strategies to promote host tolerance of allogeneic or xenogeneic transplants, such as fusing diploid somatic cells to an enucleated human or other mammalian egg and using the resultant blastocyst to make the stem cells. Such approaches trigger bioethical concerns, a problem even harder to solve.

Implantation of bioartificial tissues constructed in vitro also faces a few obstacles. For example, it remains a major challenge to synthesize scaffolding material for bionic implants that have the requisite topography, surface properties, and growth and differentiative signals to facilitate cell migration, adhesion, proliferation and differentiation, as well as being moldable into the shape of various tissues and organs. Examples of artificial biomaterials currently being used or tested include various ceramics, polyurethane elastomers, polyesters, polyanhydrides, and polyphosphazenes. These materials provide mechanical support, migration channels, and adhesive surfaces for cells.

Against this technological background briefly summarized above, the present invention provides an innovative methodology for adult tissue repair and organ regeneration. In sharp contrast to the popular approach of in vitro stem cell cultivation taken by most artisans in the field, the methodology is focused on the activation and cultivation of adult stem cells in vivo and in situ. By harnessing the body's inherent ability to repair and regenerate itself, the methodology has developed to provide optimum conditions for the body's spontaneous regeneration, a regenerative environment mimicking that needed for healthy fetal development. Inventive compositions are provided to activate dormant stem cells to proliferate or to induce conversion of adult tissue cells into regenerative stem cells, and to maintain active proliferation and directional differentiation of these stem cells into all cells needed for regeneration in vivo and in situ. Novel formulation of the active ingredients also facilitates a physiologically moist, nutritious, homeostatically balanced environment to ensure repair and regeneration of tissues and organs with complete restoration of their physiological structures and functions.

2. Regenerative Medicine for the GI Tract

Under the guidance of the fundamental principle and the methodology elucidated above, a wide variety of applications in the field of cell biology and in the practice of medicine can be envisioned. In particular, compositions are developed as pharmaceuticals or nutraceuticals for maintaining normal functions or repairing damaged mucosa and other tissues in the GI tract.

Supported by strong evidence collected in experimental models in vitro and in vivo, the inventor believes that tissue cells in any organ of a human body can be activated to produce regenerative stem cells in response to signals of tissue repair, e.g., wounds and ulcer, as long as proper regenerative conditions are provided. Unlike scarless wound healing in a fetus at its early gestation stage, physiological tissue repair and functional organ regeneration in a fully developed adult is achievable only by providing an exogeneous culture media in vivo and in situ to stimulate and maintain rapid proliferation and directional differentiation of the adult stem cells and to ensure proper assembly of various tissues organ-specifically without substantial loss in their structures and functions.

The inventor believes that although difficult to be labeled and isolated, multipotent, adult stems cells (ASCs) can be produced in vivo and in situ by activating dormant tissue stem cells and/or by inducing conversion of adult tissue cells into ASCs (FIG. 1). This belief is supported by recent advances in stem cell research and by the experimental and clinical data generated in the application of the fundamental principle elucidated in the present invention.

ASCs have been discovered recently in the liver, pancreas, and central nervous system. Mesenchymal stem cells have been isolated from the bone marrow, and there is some evidence that similar cells may even reside in the connective tissue compartments of tissues throughout the body. The locations of ASCs have been searched extensively and speculated by others to be residing in specific niches. Regardless of the precise locations of various ACS, the methods and compositions provided by the present invention can be used to activate ACSs in the body to repair damaged tissues and to regenerate dysfunctional organ in situ and in vivo. It is envisioned that this innovative methodology can be used for restoring the physiological structure and function of any tissue and any organ of the body of a mammal, preferably a human. The following section lays out the applications in the prevention and treatment of disorders in the GI tract.

In one aspect, the methodology of the present invention can be used to activate or induce regenerative stem cells in tissues in the GI tract so as to repair diseased or damaged mucosa of the organs in the tract.

In the lining of the small intestine, cells are arranged as a single-layered epithelium. This epithelium covers the surfaces of the villi that project into the lumen of the gut. Mucus-secreting goblet cells are interspersed among the adsorptive brush-border cells in the epithelium. The epithelium also lines the crypts that descend into the underlying connective tissue. It has been found that each crypt is composed of about 250 epithelial cells among which epithelial stem cells are included. These multipotent stem cells are located near or at the base of each crypt. Loeffler et al. (1993) J. Theor. Biol. 160:471-491. The intestinal epithelial stem cells response to mesenchymal cues for survive and differentiation. Normally, these cells are slowly recycling, much like the hair follicle stem cells. Some of them are converted to rapidly but transiently proliferating cells that move to the midsegment and subsequently differentiate into either the absorptive brush-border entercytes, mucus-secreting goblet cells, or enteroendocrine cells of the villi. To maintain homeostasis, the differentiated cells then die and are shed from the villi into the lumen of the gut.

As the body ages, the growth potential of intestinal epithelial stem cells is weakened; and it becomes more difficult to activate the stem cells. As a result, the ability of the intestine to maintain a healthy uptake of nutrients is compromised, leading to malnutrition, which, in turn, hastens aging.

To stop this vicious cycle, the present invention provides compositions and methods that can be used to enhance nutrient uptake of a mammal, especially a human. As described in detail in the below section of "Formulation and Routes of Administration for Tissue Repair and Organ Regeneration", the inventive compositions are highly adhesive to mucosa and can be used to deliver various nutrients and/or active ingredient(s) to stimulate ASCs for tissue repair and regeneration. When delivered orally, the composition adheres to the mucosa in the GI tract and protects the mucosa from irritation caused by consumption of alcohol, spicy food, etc. As demonstrated in the section of "Example" below, an embodiment of the inventive composition that was formulated with extract of natural products falls within the category of "generally regarded as safe". Thus, the inventive compositions can be used as nutrient supplements or nutraceuticals for a healthy person to protect the mucosa and prevent the onset of various disorders associated with damaged or weakened mucosa. Further, owing to the unique dosage form of the inventive composition, the active ingredients for stimulating regeneration of the body can be delivered in a sustained-release manner to provide constant and adequate nutrients to support and stimulate the growth of mucosal and other types of tissue cells in situ and in vivo. In addition, with rejuvenation of the aged tissue cells in the GI tract which leads to a better uptake of nutrients from food and other sources, in physiological functions of other tissues and organs of the body can also be improved through the transport of the nutrients by the blood stream.

In a related aspect, the inventive composition of the present invention can also be used for treating digestive disorders in a human patient. Digestive disorders may be a condition of a human as a result of disorders of and damage to the organs of the digestive tract or the alimentary canal, including the mouth, esophagus, stomach, and large and small intestine. Disorders of the digestive tract include peptic ulcer diseases, inflammatory bowel diseases and other insults.

One of the common causes of the disorder in the GI tract is bacterial infections caused by *Helicobacter pylori* (*H. pylori*). Infection of *H. pylori* leads to active, chronic gastritis and frequently to associated syndromes such as duodenal ulcer, gastric ulcer, gastric cancer, MALT lymphoma, or Menetrier's syndrome. Eradication or inhibition of *H. pylori* should reduce the recurrence of duodenal and gastric ulcers.

Long-standing gastritis associated with *H. pylori* infection is often associated with the expression of intestinal-like features in the gastric mucosa. This condition, referred to as intestinal metaplasia (IM), may signal an increased risk of gastric cancer, is the second leading cause of cancer related death world-wide.

The etiology of IM is unclear; it could represent a mutational adaptation or defense against *H. pylori* infection. It has been speculated that the metaplastic mucosa may produce mucus or other substances that create an environment that is hostile to *H. pylori*. Thus, widespread treatment of *H. pylori* should reduce the incidence of gastric carcinoma.

The inventor believes that the inventive composition can effectively repair the damaged mucosa by providing regenerative condition in the GI tract, especially in the stomach. Upon administration to the GI tract, the inventive composition is mixed with mucus of the stomach and forms a protective membrane containing mucin, separating the mucosa from further irritation of acid, alcohol, food and other materials contained in the stomach. Under these conditions the sterol compound and other optional active ingredients in the composition are released to the site and activate the regenerative stem cells there to promote fast healing of the mucosa. As shown in FIG. 3B the inventive composition successfully cured gastric ulcer in animal models. Further, the inventive composition may also effectively inhibit the toxicity of the bacteria *H. pylori* by changing its morphology. With the regeneration of a healthy GI tract, the ulcerous conditions that are favorable for the habitation of *H. pylori* are destroyed, thereby indirectly inhibiting the growth of the bacteria.

The methods and composition of the present invention can be used in the treatment of *H. pylori* infection and conditions associated with *H. pylori* infection (e.g., ulcers, gastric carcinoma, non-ulcer dyspepsia, gastritis, and esophageal lesions associated with gastro-esophageal reflux disease). The inventive composition is useful for treatment of these conditions because of its generally protective effect on the gastrointestinal (GI) tract. In addition, it promotes the maintenance of mucosal integrity.

The inventive composition of the present invention can be used to inhibit adhesion to or colonization of the mucosa by *H. pylori*. It may also be used promote healing of tissues damaged by conditions associated with *H. pylori* infection. In this regard, it is presumed that addition of the inventive composition to wounded monolayers of confluent intestinal epithelial cells activates epithelial stein cells in the crypts and increases the rate of epithelial cell migration into the wound.

Just as the inventive composition can be used to protect other parts of the gastrointestinal tract or alimentary canal, such as the intestine, it can be used to protect the mouth and esophagus from damage caused by radiation therapy or chemotherapy. Radiation and systemic administration of anticancer drugs have cytotoxic effects on fast proliferative cells such as lymphocytes, mucosal cells and hair cells, leading to myelosuppression, mucositis, and alopecia, respectively. These side effects of anticancer therapy not only significantly lower the patient's quality of life but also cause a lot of pain and suffering in the patient and his/her family. In particular, damages to the mucosa result in a poor uptake of nutrients which are needed for boosting the body's immune system to fight the cancer. Thus, by using the inventive composition of the present invention, the damaged mucosa may be repaired and its physiological functions be restored, thereby indirectly inhibiting the growth and metastasis of cancer.

In yet another aspect, the methodology and inventive compositions of the present invention may be used for treating or preventing hyperproliferative diseases or pre-cancerous conditions affecting epithelial cells of the internal organs, such as organs in the gastrointestinal (GI) tract. Administration of the inventive composition orally may restore the homeostatic balance of these organs by reestablishing the cell-cell crosstalk between the precancerous cells with the healthy cells of the host.

Cancer is generally viewed as the result of disrupted intra- and intercellular homeostatic regulation. Once the homeostatic balance is lost and malignant transformation has occurred, microenvironment factors such as degradation of matrix components and host-tumor interactions are essential for survival and growth of the malignant cells.

By using the inventive compositions and methods, the homestatic balance of tissues may be restored without loss of physiological functions. As demonstrated in the below section of "Example", the ability of the inventive composition to promote growth of intestinal and gastric cells to form tissues in vitro indicates that the inventive composition likely is able to regulate intercellular communication and promote cell-cell interactions by stimulating cross-talk mediated by various cell membrane proteins such as connexins and cadherins. This results in a coordinated regulation of cell growth, differentiation, apoptosis and migration.

The inventive composition may assert its function of restoring tissue homestatic balance through promoting the formation of gap junctions between precancerous or cancer cells and the host cells. Gap junctions are a unique type of intercellular junction found in most animal cell types. Two adjacent cells interact with each other through the cell membrane proteins, connexins, which form the gap junction. Six identical connexins from a connexon; two connexons join across the intercellular gap to form a continuous aqueous channel connecting the two cells. Each gap junction is a cluster of homogeneous intramembrane particles associated with the cytoplasmic fracture face of the plasma membrane. Each intramembrane particle corresponds to a connexon. Gap junctions permit the intercellular passage of small molecules and have been implicated in diverse biological processes, such as development, cellular metabolism, and cellular growth control.

The majority of connexins are modified posttranslationally by phosphorylation, primarily on serine amino acids. Connexins are targeted by numerous protein kinases, of which some have been identified: protein kinase C, mitogen-activated protein kinase, and the v-Src tyrosine protein kinase. Phosphorylation has been implicated in the regulation of a broad variety of connexin processes, such as the trafficking, assembly/disassembly, degradation, as well as the gating of gap junction channels.

In addition, another cell membrane protein cadherin also plays important role in cell-cell adhesion and migration. It has been found that cadherin-mediated cell-cell adhesion is perturbed in protein tyrosine kinase (PTK)-transformed cells. While cadherins themselves appear to be poor PTK substrates, their cytoplasmic binding partners, the Arm catenins, are excellent PTK substrates and therefore good candidates for mediating PTK-induced changes in cadherin behavior. For example, beta-catenin binds to the cytoplasmic region of classical cadherins and function to modulate adhesion and/or bridge cadherins to the actin cytoskeleton.

It is likely that the inventive composition activates these kinases which then phosphorylate connexins and the cellular binding partners of cadherins such as catenins. Through proper phosphorylation of these proteins associated with cell-cell adhesion, the communication channels between the tumor cells and the host cells are restored. With the restoration of tumor-host connection, the tumor cells are subjected to the regulation of the host. Under the regulation of the host, the tumor cells may be induce to undergo apoptosis (programmed cell death) or differentiate to become non-tumorigenic. Thus, the homeostatic balance of the tissue is restored to prevent or inhibit malignancy of tumors.

In a particular aspect, the methodology of the present invention is used for treating cancer in the upper and lower GI tract. Examples of upper GI cancer include, but are not limited to, 1) esophagus cancer caused by excessive alcohol use, lye ingestion, achalasia, cigarette smoking, exposure to nitroamine, Barrett's mucosa, tylosis, mycotoxin, infection with transforming viruses such as human pappiloma virus (HPV), herpes simplex virus (HSV), cytomegalovirus (CMV) and Epson-Barr virus (EBV), Plummer Vinson Syndrome; 2) stomach cancer caused by achlorhydria, *Helicobacter pylori* infection, previous gastrectomy, and Billroth II procedure; 3) pancreas cancer caused by cigarette smoking, exposure to beta-naphthylamine, benzidine, and chronic pancreatis; 4) liver cancer caused by hepatitis B virus, chronic liver diseases such as chronic active hepatitis and cirrhosis, exposure to mycotoxin, ionizing radiation, steroid hormones and arsenic; and 5) cancer of bile ducts caused by sclerosing cholangitis, parasitic infections and steroid hormones. Examples of lower GI cancer includes cancers of the large bowel such as colorectal carcinoma, primary lymphomas, melanoma, and sarcoma of the large bowel. Adenocarcinomas account for more than 90% of large bowel cancers. Cancinoid tumors account for most of the rest of malignant neoplasma arising in the colorectum.

3. Formulation and Routes of Administration for Tissue Repair and Organ Regeneration The present invention provides novel compositions for pharmaceutical or nutraceutical use in an animal, preferably in a human. A pharmaceutical is a composition that is used as a medicament to cure a disease condition with or without a physician's prescription. A nutraceutical is a composition that is used as a nutritional supplement for promoting general health or to remedy a particular condition of the body. Nutraceuticals are usually sold in health food stores and supplied without a physician's prescription.

In one aspect, the compositions are provided for promoting cell growth, tissue repair and organ regeneration, preferably in vivo. It should be noted the compositions may be adapted for use in vitro as cell growth culture media or in ex vivo reconstruction of tissues and/or organs.

In particular, the compositions are provided for repairing and promoting regeneration of mucosa in the GI tract in order to restore physiological structure and function to the damaged or dysfunctional mucosa, to enhance the body's ability to absorb nutrients, to achieve healthy and balanced metabolism, and ultimately to promote the general health of the whole body. It should be noted that the compositions may be adopted for use in the treatment of dysfunctional mucosa of other organs, such as nasal, lung, anal, vaginal, aural, eye, and oral mucosa.

In one embodiment, a composition suitable for oral administration is provided for promoting mucosal cell growth in the GI tract. The composition is in an oral dosage form and comprises: an edible oil homogenized with an edible wax at a concentration ranging from 0.5% to 50% by weight and a sterol compound at a concentration of at least 0.1% by weight.

The concentration of the sterol compound preferably ranges from about 0.5% to 20% by weight, more preferably about 1% to 10% by weight, and most preferably about 2% to 6% by weight.

The concentration of the edible wax preferably ranges from about 3% to 30% by weight, more preferably about 5% to 20% by weight, and most preferably about 6% to 10% by weight.

The sterol compound may be an animal sterol or a plant sterol (also called phytosterol). Examples of animal sterol include cholesterol and all natural or synthesized, isomeric forms and derivatives thereof. Preferably, the sterol compound is selected from the group consisting of stigmasterol, campesterol, β-sitosterol, chalinosterol, clionasterol, brassicasterol, α-spinasterol, dancosterol, desmosterol, poriferasterol, and all natural or synthesized, isomeric forms and derivatives thereof. More preferably, the sterol compound is a combination of stigmasterol, β-sitosterol, and campesterol, collectively referred to herein as "sitosterol".

Not wishing to be bound by the theory as to the mechanism of action of the sterol compound in tissue repair and organ regeneration, the inventor believes that the sterol compound may play important roles in inducing morphogenesis of the cells by changing the fluidity and permeability of the cell membrane. As a result, many cell membrane-associated proteins such as kinases and phosphotases may be activated to stimulate cell growth. It is also plausible that dormant stem cells may be activated due to morphogenic changes in the membrane. Further, differentiated adult tissue cells may also be induced to undergo transformation into a non-differentiated phenotype, i.e., the process called "dedifferentiation". With the change of permeability of the cell membrane, other mitogens and regulatory molecules may be more readily uptaken by the cells so as to stimulate a balanced growth of a wide variety of cells needed for physiological tissue repair and functional organ regeneration. Moreover, expression and phosphorylation of cell adhesion molecules (CAMs) may be stimulated, presumably due to activation of membrane-bound proteins during the morphogenesis process, thus further enhancing association of cognate cells to form a specific tissue, and assembly of cognate tissues to form a fully functional organ within the body. In addition, production of prostaglandin (PG) may be stimulated by the sterol compound, which, in turn, can stimulate secretion of gastric mucus to form an effective barrier to resist irritation to the mucosa.

It is to be understood that modifications to the sterol compound i.e. to include side chains also fall within the purview of this invention. It is also to be understood that this invention is not limited to any particular combination of sterols forming a composition. In other words, any sterol compound alone or in combination with other sterol compound in varying ratios as required depending on the nature of the ultimate formulation fall with the purview of this invention.

The sterol compound for use in this invention may be procured from a variety of natural sources. For example, phytosterol may be obtained from the processing of plant oils (including aquatic plants) such as corn oil, wheat germ oil, soy extract, rice extract, rice bran, rapeseed oil, sesame oil, and other vegetable oils, and fish oil. Without limiting the generality of the foregoing, it is to be understood that there are other sources of phytosterols such as marine animals from which the composition of the present invention may be prepared. For example, phytosterols may be prepared from vegetable oil sludge using solvents such as methanol. Alternatively, phytosterols may be obtained from tall oil pitch or soap, by-products of the forestry practice.

The edible oil may be any natural or synthetic oil suitable for oral administration to a human. Examples of natural oil include, but are not limited to, corn oil, wheat germ oil, soy bean oil, rice bran oil, rapeseed oil, sesame oil, fish oil and other vegetable and animal oils.

The edible wax may be any wax suitable for oral administration to a human, either natural or synthetic. Examples of edible wax include, but are not limited to, beeswax, castorwax, glycowax, and carnaubawax.

Figure 4A:
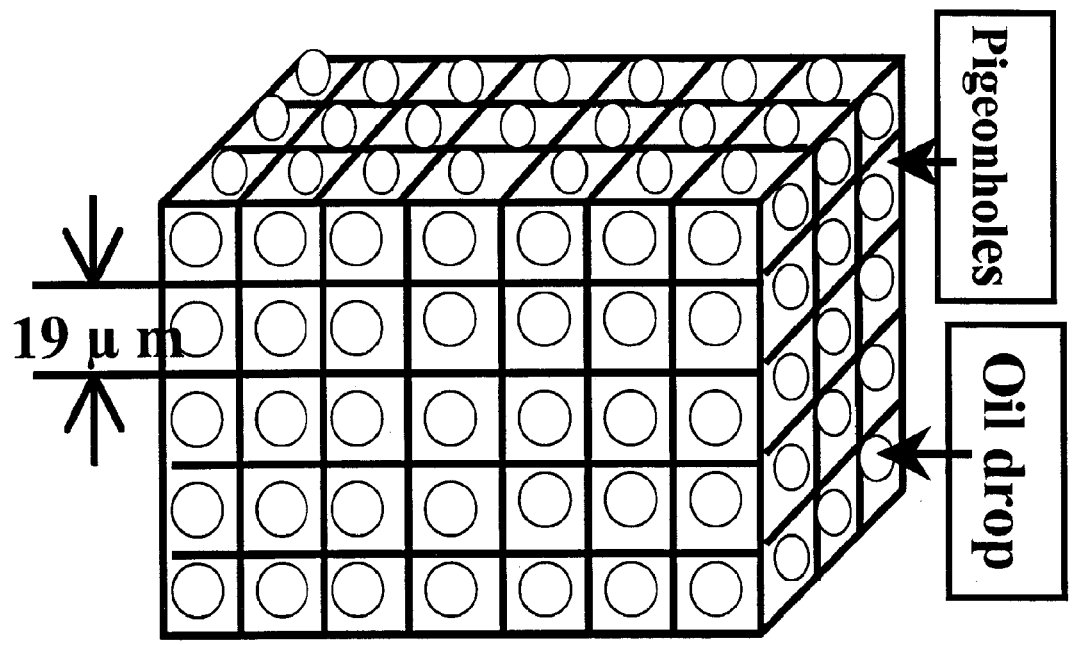
FIG. 4A shows a model for a pigeonhole structure adopted by beeswax when mixed sesame oil without homogenization.
Figure 4B:
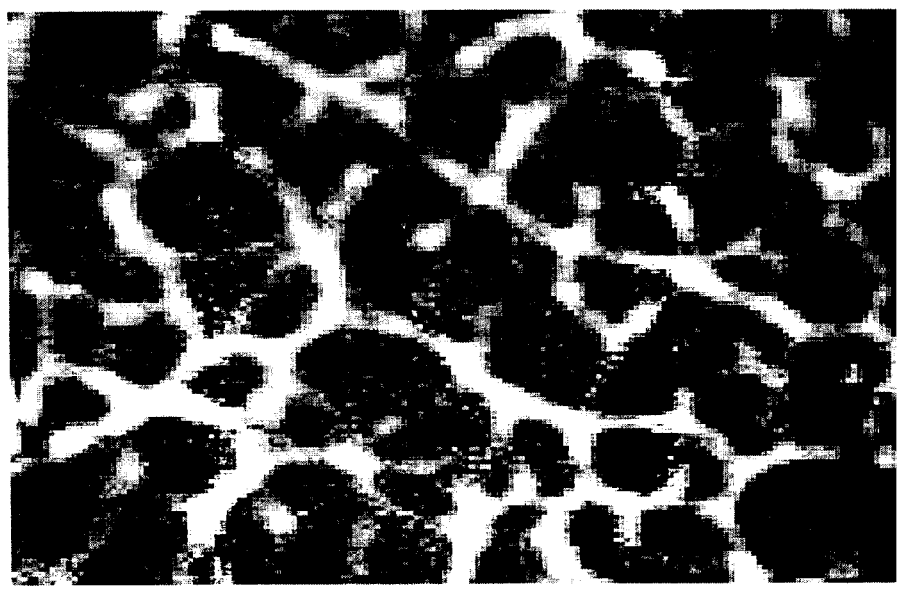
FIG. 4B shows an eletrograph of beeswax when mixed sesame oil without homogenization.

The edible wax, for example beeswax, usually has a higher melting point than the edible oil (e.g., sesame oil). Beeswax is solid at room temperature and melts when heated to about 70-80° C. When melted, the wax can be mixed with the oil with adequate stirring. However, when the mixture of beeswax and sesame oil is allowed to cool down to ambient temperature (i.e., 20-25° C.), beeswax cools down much faster than the oil due to their differential thermo-physical properties. As a result, the solidified wax forms a 3-dimensional structure with small "pigeonholes" within which oil drops are enclosed. FIG. 4A illustrates a model structure with beeswax forming the pigeonholes and oil drops enclosed therein. FIG. 4B shows an electronograph of a mixture comprising about 10% beeswax and about 90% sesame oil. As shown in FIG. 4B, beeswax forms a three-dimensional pigeonhole-like structure with the dimension of the holes averaged at 19 µm and has individual oil drops enclosed therein.

By comparison, when the mixture of beeswax and sesame oil is homogenized in a mixer of standard type, a much even distribution of the wax is achieved. Homogenization of the wax and oil may be achieved by emulsification with a homogenizer or a colloid mill. A colloid mill is preferred since it is capable of providing both shear forces and back pressure through a continuously circulating milling process.

Figure 5A:
FIG. 5A shows a micrograph of beeswax when homogenized with sesame oil, showing single, needle-like microcrystals of beeswax.
Figure 5B:
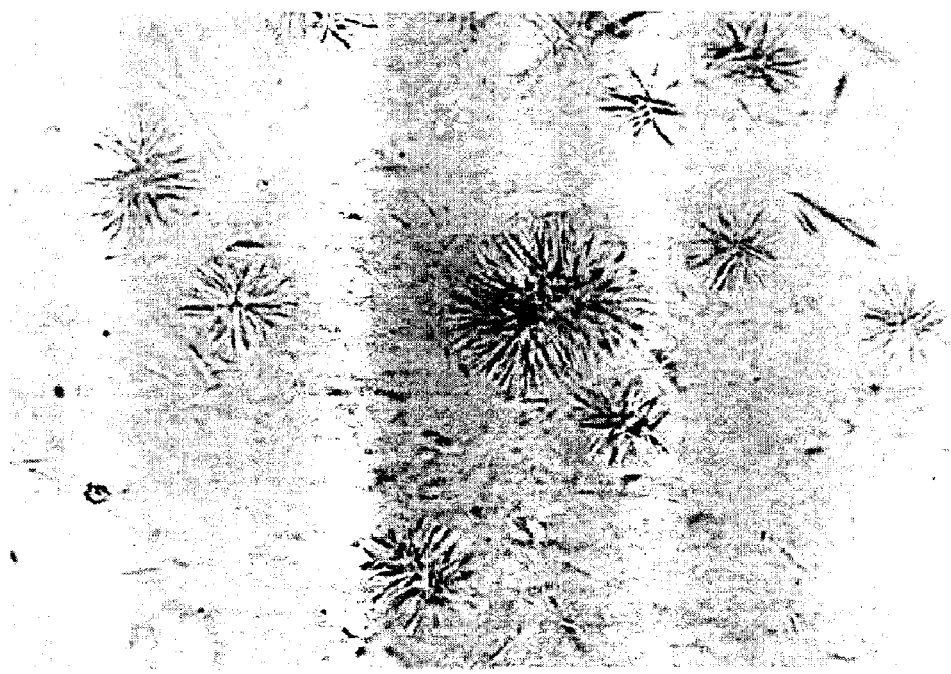
FIG. 5B shows a micrograph of beeswax when homogenized with sesame oil, showing microcrystal complexes of beeswax.

Observed with naked eyes, the homogenized mixture of beeswax and sesame oil appears to adopt a colloidal form. Examined under a microscope at ambient temperature, discrete microcrystals of beeswax form and distribute more or less uniformly throughout the texture. FIGS. 5A-B are micrographs showing the microcrystals of beeswax in an embodiment of the composition comprising about 7% of beeswax homogenized with about 92% of sesame oil. As shown in FIGS. 5A-B, there are two major forms of the microcrystals: needle-like microcrystals (FIG. 5A) and microcrystal complexes in bundles or in various asterisk shapes (FIG. 5B). In contrast to the mixture show in FIG. 4B where oil drops are enclosed in the "pigeonhole" structure formed by beeswax, here microcrystals of beeswax are dispersed in the oil quite uniformly without forming a connected 3D network structure. The size of the needle-like microcrystal varies from small (e.g., 7 µm in length and 0.4 µm in width), medium (e.g., 28 µm in length and 0.6 µm in width), to large (e.g., 52 µm in length and 0.8 µm in width). The size of the microcrystal complexes varies from small (e.g., 18 µm in diameter), medium (e.g., 36 µm in diameter), to large (e.g., 50 µm in diameter).

Surprisingly, this unique feature of the composition formed by homogenizing the wax and the oil confers a superior ability to the composition to adhere to mucosa and a much higher efficacy in the treatment of acute ulcer caused by alcohol in animal models. In a laboratory study, seven rats in the control group to which only water was given developed ulcer after being gavaged with anhydrous alcohol with the ulcer area averaged at 68 $mm^2$. The composition wherein beeswax adopts the pigeonhole structure (FIG. 4B) could not protect rats from developing gastric ulcer with just one time administration of the composition to the rats (number=7) 2 hours before being gavaged with anhydrous alcohol. Ulcer developed in these rats with the ulcer area averaged at 110 $mm^2$. Instead, multiple rounds of administration (once a day for three days) were needed to prevent ulcer development in the rats (number=8). In contrast, the composition with microcrystals of beeswax distributing evenly throughout the colloidal texture was very effective in preventing ulcer development in the rats (number=8) with just one time administration of the composition 2 hours before gavaging with anhydrous alcohol. The average ulcer area in these rats was about 15 $mm^2$, 7 folds less than that in rats treated with the composition wherein beeswax adopts the pigeonhole structure under the same conditions of the treatment.

These results indicate that the inventive composition with the wax homogenized with the oil is particularly effective in adhering to mucosa in the GI tract and protecting it from the ulcerous effects of alcohol. In comparison, the composition wherein beeswax adopts the pigeonhole structure with oil drops enclosed is presumed to adhere poorly and/or too slowly to the gastric mucosa before being exposed to alcohol.

Not wishing to be bound by the theory, the inventor believes that the microcrystals of beeswax may be able to mix more readily with mucus in the GI tract than beeswax in large particles or adopting a pigeonhole structure. It is also likely that in mixing with mucus, the microcrystals of beeswax induce the formation of an artificial membrane in a colloidal form to overlay the mucosa, thus protecting it from the ulcerous effects of alcohol. By adhering to the mucosa surface tightly, this artificial membrane may be able to improve microcirculation, to expand local mucous membrane capillary vessel, to accelerate circulation of blood and lymph, and to promote active metabolism of connective tissues. Moreover, with the gradual erosion of this artificial membrane in the stomach active ingredients trapped in the colloid can be released slowly to the mucosa and its underlying tissues. Such a sustained release should be advantageous in the delivery of active ingredients to stimulate growth of mucosal and other tissue cells for repair and regeneration.

For maintaining structural integrity and chemical stability, the composition contains minimum amount of water, preferably less than 1% by weight, more preferably less than 0.1% by weight, and most preferably less than 0.01% by weight.

Other than providing a structural support for the adhesion of the inventive composition to the mucosa, beeswax also possesses many beneficial biochemical properties. Beeswax has long been used as an excipient for manufacturing drugs for external use. In traditional Chinese medicine, beeswax is a drug for detoxication, granulation promotion, for relieving pain and cardialgia and treating diarrhea, pus and bloody stool, threatened abortion with vaginal bleeding, septicemia, refractory ulcer and thermal injury ("A Dictionary of Chinese Materia Medica", in Chinese, "Zhong Yao Da Ci Dian", Science and Technology Press, Shanghai, 1986, page 2581).

The constituents of beeswax can be grouped into four categories, i.e., esters, free acids, free alcohols and paraffins. Beeswax also contains trace amount of essential oil and pigment. Among the esters, there are myricyl palmitate, myricyl cerotate, and myricyl hypogaeate. In free acids, there are cerotic acid, lignoceric acid, montanic acid, melissic acid, psyllic acid, hypogaeic acid and neocerotic acid. Among free alcohols, there are n-octacosanol and myricyl alcohol and in the paraffins, pentacosane, heptacosane, nonacosane and hentriacontane, and an olefin called melene. An aromatic substance called cerolein is also found in beeswax.

Not wishing to be bound by the theory, the inventor believes that these ingredients of beeswax, once released from the artificial membrane formed by the inventive composition on the mucosa, may have many beneficial effects on the body. These ingredients of beeswax may also act in synergy with the active ingredients in the inventive composition (e.g., the sterol compound) to further promote general health and to cure various disorders of the body. For example, some ingredients may be able to enhance the phagocytic capacity of the mononuclear macrophage system as well as the permeability of histiocyte and body metabolism. Some ingredients in beeswax may also have anti-inflammatory and anti-ulcer effects. Octacosane alcohol contained in beeswax may be beneficial in reinforcing stamina, energy, and strength; enhancing muscle strength, increasing the reflex sensitivity; enhancing the body's ability to resist irritations from harmful substances; accelerating sex hormone secretion; inhibiting jerk; improving muscle and cardiac muscle function; and reducing systolic pressure and increase basal metabolic rate.

The composition may further comprise propolis at a concentration ranging from about 0.1% to 30% by weight, more preferably from about 1% to 20% by weight, and most preferably from about 5% to 10% by weight.

Propolis is known as a sticky, gum-like substance which is used to build the beehives. In intact propolis a variety of trace ingredients in form of a homogenous mixture with resins, beeswax, essential oils and pollens as predominant ingredients, as well as other ingredients such as flavonoids and phenol carboxylic acids. Natural propolis hardly dissolves in water and has a peculiar odor. Propolis can be prepared from beehives by extraction with organic solvents such as ethonol, ether and chloroform. The ingredient contained in propolis may have the activity of resisting pathogenic micro-organism and anti-protoplast, enhancing immunologic function of human body, and promoting tissue regeneration and anti-oxidation.

The edible oil in the composition acts as a solvent to dissolve active ingredients and to disperse beeswax particles or microcrystals. Sesame oil is preferably used for formulating the composition. Not wishing to be bound by the theory, the inventor believes that sesame oil may have the following beneficial effects on the body: 1) loosing the bowel to relieve constipation; 2) resisting inflammation, anti-infection, promoting tissue repair; 3) directly protecting gastric mucous membrane; 4) indirectly protecting gastric mucous membrane and against ulcers by accelerating gastric mucus secretion with oleic acid and linoleic acid contained in sesame oil; 5) antioxidation activity of ingredients contained in sesame oil including sesamol and Vitamin E which have strong anti-oxidation activity to eliminate free radical, protect the structure and function of the biomembrane, and protect gastrointestinal mucous membrane; 6) sesamin contained in sesame oil having effects of promoting metabolism of normal cell; 7) providing nutrition such as amino acids, lipids and microelement that are necessary for the repair of gastrointestinal mucous membrane; and 8) acting as excipient to reduce irritation of drugs and the impact of stomach evacuation and food on therapeutic efficacy of drugs.

For oral administration, the inventive composition can be formulated readily by combining with pharmaceutically acceptable carriers that are well known in the art. Such carriers enable the compounds to be formulated as tablets, pills, dragees, capsules, emulsions, gels, syrups, slurries, suspensions and the like, for oral ingestion by a patient to be treated.

In a preferred embodiment, the inventive composition is contained in capsules. Capsules suitable for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. More preferably, the inventive composition is contained in soft capsules. The inventive composition may be dissolved or suspended in suitable liquids, such as fatty oils or liquid polyethylene glycols. In addition, stabilizers may be added. All formulations for oral administration should be in dosages suitable for such administration.

Optionally, the inventive composition for oral use can be obtained by mixing the inventive composition with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The inventive composition may further comprise baicalin, preferably at a concentration ranging 0.01 to 5% by weight, more preferably about 0.1 to 2% by weight, and most preferably about 0.1% to 1% by weight.

Not wishing to be bound by the theory, it is believed that baicalin may have anti-inflammatory effects on the damaged or diseased tissue, which helps providing a low inflammation environment for organ regeneration, mimicking that in scarless wound healing of a fetus at its early gestation stage. It might also be possible that baicalin may bind to cell membrane receptors for polysaccharides such as selectin and further promote cell adhesion. Other beneficial effects of baicalin include: 1) anti-inflammation; 2) anti-allergy; 3) anti-lipid peroxidation, presumably by inhibiting the formation of peroxide lipid and eliminating free radicals; 4) inhibiting platelet agglutination and accelerating blood circulation; 5) inhibiting spasm of intestinal smooth muscle and improving function of smooth muscle; 6) anti-pathogenic micro-organism such as bacteria, fungus and virus; and 7) detoxifcation, resulting in reduction in the intensity of spasm and decrease in mortality.

Baicalin may be obtained by extracting huangqin (*Radix Scutellariae*) in aqueous solution, oil, alcohol or other organic solvent, preferably in oil at temperature higher than 100° C., more preferably between about 120-200° C., and most preferably between about 160-180° C. Preferably, the root of huangqin is used and may be obtained from the plant selected from one or more members of the group of *Scutellaria viscidula* Bge, *Scutellaria amoena* C. H. Wright, *Scutellaria rehderiana* Diels, *Scutellaria ikonnikovii* Juz, *Scutellaria likiangensis* Diels and *Scutellaria hypericifolia* Levl of Labiatae Family. Dictionary of Chinese Materia Medica, Shanghai Science and Technology Press, 1988, pages 2017 to 2021.

The inventive composition may further comprise obaculactone (also called limonaic acid), preferably at a concentration ranging from about 0.01 to 5% by weight, more preferably about 0.1 to 2% by weight, and most preferably about 0.1% to 1% by weight. Obaculactone may be obtained by extracting huangbai (*Phellodendron amurense* Rupr) in oil, alcohol or other organic solvent, preferably in oil at temperature higher than 100° C., more preferably between about 120-200° C., and most preferably between about 160-180° C. Alternatively, obaculactone may also be obtained by extracting huangbai in alcohol such as ethanol. Preferably, the bark of huangbai is used and may be obtained from the plant selected from one or more members of the group of *Phellodendron chinense Schneid, Plellodendron chinense Scheid var. glabriusculum Schneid, Phellodendron chinense Schneid var. omeiense Huang, Phellodendron Schneid var. yunnanense Huang and Phellodendron chinense Schneid var. falcutum Huang*. A Dictionary of Chinese Materia Medica, Shanghai Science and Technology Press, 1988, pages 2031 to 2035.

Optionally, the inventive composition may further comprise obabenine, preferably at a concentration ranging from about 0.001% to 2% by weight, more preferably about 0.002% to 0.5% by weight, and most preferably about 0.003% to 0.1% by weight.

Obabenine may be obtained by extracting huangqin, huangbai, and/or huanglian (coptis chinensis Franch) in aqueous solution, oil, alcohol or other organic solvent. Root of huanglian is preferably used. Huanglian may be selected one or more from the group of *Coptis deltoidea* C. Y. Cheng et Hsiao, *Coptis omeiensis* (Chen) C. Y. Cheng, and *Coptis teetoides* C. Y. Cheng of Ranunculaceae Family. A Dictionary of Chinese Materia Medica, Shanghai Science and Technology Press, 1988, pages 2022 to 2030.

Also optionally, the inventive composition may further comprise berberine, preferably at a concentration ranging from about 0.001% to 2% by weight, more preferably about 0.002% to 0.5% by weight, and most preferably about 0.003% to 0.1% by weight.

Also optionally, the inventive composition may further comprise narcotoline, preferably at a concentration ranging from about 0.001% to 2% by weight, more preferably about 0.002% to 0.5% by weight, and most preferably about 0.003% to 0.1% by weight.

Obabenine, berberine and narcotoline alone or in combination may suppress pain in the damaged tissue by inhibiting smooth muscle contraction.

Optionally, the inventive composition may further comprise various amino acids, preferably all 18 natural amino acids, for providing nutrition support to cell growth. The amino acids may be chemically synthesized or obtained from natural sources. For example, a full spectrum of natural amino acids may be obtained by extracting earthworms, a rich source of protein/amino acids, in oil or alcohol. The inventive composition may further comprise nucleic acid bases such as adenine, cytidine, guanine, thymine and uridine.

In another aspect, the present invention provides methods for protecting and repairing mucosa, presumably by promoting the growth of regenerative mucosal cells. By using these methods, physiological structure and function of the damaged or dysfunctional mucosa may be restored to enhance the body's ability to absorb nutrients, which, in turn, can improve the body's general health and strength the immune system to fight diseases.

In yet another embodiment, a method is provided for preventing ulceration or irritation of mucosa in the gastrointestinal tract of a host. The method comprises: orally administering to the host a composition comprising an edible oil homogenized with an edible wax at a concentration ranging from 0.5% to 50% by weight and a sterol compound at a concentration of at least 0.1% by weight.

According to this embodiment, the host is preferably a human. As a prophylaxis, the composition may be administered to the host prior to consumption of alcohol, spicy food or other irritants to the stomach. Alternatively, the composition may be administered to the host post consumption of these irritants to the stomach.

In yet another embodiment, a method is provided for treating a host having a gastrointestinal disorder. The method comprises: orally administering to a host having a gastrointestinal disorder a composition comprising an edible oil homogenized with an edible wax at a concentration ranging from 0.5% to 50% by weight and a sterol compound at a concentration of at least 0.1% by weight.

According to this embodiment, the host is preferably a human. The composition may be used as a pharmaceutical, a nutraceutical or a health food with or without a physician's prescription. The dosing regimen may vary depending on the severity of the condition of the host. The composition is preferably administered in an amount of 0.5-10 g per day, more preferably 2-8 g per day, and most preferably 3-6 g per day. For example, if the composition is supplied as 0.5 g soft gel capsules, 1-10 capsules may be administered twice a day.

Examples of the gastrointestinal disorder include, but are not limited to, gastrointestinal diseases, such as acute gastritis, chronic superficial gastritis, atrophic gastritis, antral gastritis, senile gastritis, bile-regurgitational gastritis, esophagitis, gastroduodenal ulcer, indigestion, gastric neurosis, constipation, as well as various consequent conditions including gastric hyperacidity, hypochlorhydria, flatulency, gastrointestinal discomfort after meals, gastritis caused by taking acidic drugs such as salicylates (e.g., aspirin), gastric discomfort after drinking, and gastric discomfort due to fasting.

In yet another embodiment, a method is provided for treating a patient having a gastrointestinal cancer. The method comprises: orally administering to a patient having a gastrointestinal cancer a composition comprising an edible oil homogenized with an edible wax at a concentration ranging from 0.5% to 50% by weight and a sterol compound at a concentration of at least 0.1% by weight.

The gastrointestinal (GI) cancer can be an upper or lower GI cancer. Examples of the upper GI cancer include, but are not limited to, 1) esophagus cancer; 2) stomach cancer; 3) pancreas cancer; 4) liver cancer; and 5) cancer of bile ducts. Examples of the lower GI cancer include, but are not limited to, cancers of the large bowel such as colorectal carcinoma, primary lymphomas, melanoma, and sarcoma of the large bowel.

Also optionally, the inventive composition may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the inventive compositions for a few weeks up to over 100 days.

4. Delivery Vehicle for Oral Administration of Pharmaceuticals

Based on the unique physical and biochemical property of the composition formed by homogenizing an edible wax (e.g., beeswax) and an edible oil (e.g., sesame oil), a pharmaceutical delivery vehicle is provided for orally delivering a drug. The pharmaceutical delivery vehicle comprises: an edible oil homogenized with an edible wax at a concentration ranging from 0.5% to 50% by weight, wherein the edible wax forms microcrystals which are dispersed substantially uniformly in the edible oil at ambient temperature.

The size of the microcrystal is preferably between 0.1-100 µm, more preferably 5-70 µm, and most preferably 10-50 µm in length. The form of the microcrystals may vary depending on the concentration and temperature. At ambient temperature, the microcrystal may adopt a single, needle-like crystal form and/or form a microcrystal complex by aggregating with each other.

The composition may further comprise a sterol compound at a concentration preferably ranging from about 0.1% to 20% by weight, more preferably about 1% to 10% by weight, and most preferably about 2% to 6% by weight.

As described above in the section of "Formulation and Routes of Administration for Tissue Repair and Organ Regeneration", the microcrystals of beeswax dispersed in sesame oil have a superior ability to adhere to mucosa and allow a sustained release of active ingredients dissolved in the oil or entrapped in the microcrystals to reach mucosa and other tissues underneath. Further, owing the strong resistance of beeswax and sesame oil to acid and oxidation, the active ingredients included in the composition can be protected from decomposition in the acidic and oxidative environment of the stomach. These features are advantageous and desirable not only in enhancing the bioavailability but also in raising the therapeutic index of the active ingredient.

A wide variety of drugs can be formulated in the pharmaceutical base provided above. Preferably, the drugs are suitable for oral administration. However, those drugs in other formulations that are deemed unsuitable for oral administration due to poor bioavailability may also be candidates for the combination with the pharmaceutical delivery vehicle of the present invention if such a combination results in improved bioavailability of the drugs.

The drug may be in the class of 1) gastrointestinal agents; 2) antibiotics; 3) antiviral agents; 4) antifungal agents 5) antineoplastic agents; 6) analgesics; 7) tranquilizers; 8) narcotic antagonists; 9) antidepressants; 10) antihistamines; 11) antimigraine; 12) cardiovascular drugs; 13) calcium channel blockers; 14) appetite suppressant; 15) contraceptive agents; 16) corticosteroids; 17) local anaesthetics; 18) diuretics; 19) antihypertensive agents; 20) steroids; 21) prostaglandins; 22) anti-inflammatory drugs; 23) antithrombotic agents; 24) cardiac glycosides; 25) antiparkinsonism; 26) chemical dependency drugs; 27) acidic drugs; and 28) peptides;

Examples of gastrointestinal agents include, but are not limited to, histamine H2 receptor antagonists such as nizatidine, famotidine, cimetidine, ranitidine, laxatives such as docusate sodium, bisacodyle, and antiemetics such as meclizine, metoclopramide, droperidol, haloperidol, and promethazine.

Examples of analgesics include, but are not limited to, buprenorphine, codeine, fentanyl, morphine, and hydromorphone.

Examples of anti-inflammatory drugs include, but are not limited to, ibuprofen, indomethacin, naproxen, diclofenac, tolfenamic acid, and piroxicam.

Examples of tranquilizers include, but are not limited to, diazepam, droperiodol, fluspirilene, haloperidol, and lorazepam.

Examples of cardiac glycosides include, but are not limited to, digoxin and ouabain, Examples of narcotic antagonists include, but are not limited to, naloxone, and nalorphine.

Examples of antiparkinsonism agents include, but are not limited to, bromocriptine, biperidin, benzhexol, and benztropine.

Examples of antidepressants include, but are not limited to, imipramine, nortriptyline, and pritiptylene.

Examples of antineoplastic agents include, but are not limited to, bleomycin, cyclosporin A, fluorouracil, mercaptopurine, methotrexate, camptothecin, paclitaxel, doxorubicin, and mitomycin.

Examples of antiviral agents include, but are not limited to, idoxuridine, acyclovir, interferons, AZT, and vidarabin.

Examples of antibiotic agents include, but are not limited to clindamycin, erythromycin, fusidic acid, gentamicin, and tetracyclin.

Examples of antifungal agents include, but are not limited to miconazole, ketoconazole, metronidazol, clotrimazole, amphotericin B, and nystatin.

Examples of appetite suppressants include, but are not limited to, fenfluramine, mazindol, and phentermin.

Examples of antihistamine include, but are not limited to, chlorpheniramine, terfenadine, and triprolidine.

Examples of antimigraine agents include, but are not limited to, dihydroergotamine, ergotamine, and pizotyline.

Examples of cardiovascular agents include, but are not limited to, nifedipine, diltiazem, glyceryl nitrate, isosorbide dinitrate, molsidomine, verapamil, and the like;

Examples of calcium channel blockers include, but are not limited to, verapamil, nifedipine, diltiazem, and nicardipine.

Examples of steroids include, but are not limited to, estradiol, estron, estriol, polyestradiol, polyestriol, dienestrol, diethylstilbestrol, dihydroergosterone, cyproterone, danazol, testosterone, progesterone, norethindrone, levonorgestrol, ethynodiol, norgestimate, gestanin, 3-keton-desogestrel, demegestone, promethoestrol, testosterone, spironolactone, and esters thereof;

Examples of antithrombotic include, but are not limited to, heparin, and warfarin.

Examples of diuretics include, but are not limited to, hydrochlorothiazide, flunarizine, and minoxidil.

Examples of antihypertensive agents include, but are not limited to, propanolol, metoprolol, clonidine, and pindolol.

Examples of chemical dependency drugs include, but are not limited to, nicotine, and methadone.

Examples of local anaesthetics include, but are not limited to, lidocaine, prilocaine, and benzocaine.

Examples of corticosteroids include, but are not limited to, beclomethasone, betamethasone, clobetasol, desonide, desoxymethasone, dexamethasone, diflucortolone, flumethasone, fluocinolone acetonide, fluocinonide, hydrocortisone, methylprednisolone, triamcinolone acetonide, budesonide, and halcinonide.

Examples of acidic drugs include, but are not limited to, salicylates such as aspirin.

Examples of peptides include, but are not limited to, growth hormone releasing factors, growth factors (epidermal growth factor (EGF), nerve growth factor (NGF), TGF, PDGF, insulin growth factor (IGF), fibroblast growth factor (aFGF, bFGF. etc.), and the like), somatostatin, calcitonin, insulin, vasopressin, interferons, IL-2, urokinase, serratiopeptidase, superoxide dismutase (SOD), tryrotropin releasing hormone (TRH), luteinizing hormone releasing hormone (LH-RH), corticotrophin releasing hormone (CRF), growth hormone releasing hormone (GHRH), oxytocin, erythropoietin (EPO), and colony stimulating factor (CSF).

Other specific examples of active ingredients for use according to the invention include azole derivatives such as, e.g., imidazoles and mazoles and derivatives thereof; nitro compounds such as, e.g., amyl nitrates, nitroglycerine and isosorbide nitrates; amine compounds such as, e.g., pilocaine, oxyabutyninchloride, lidocaine, benzocaine, nicotine, chlorpheniramine, terfenadine, triprolidine, propanolol, metoprolol and salts thereof; oxicam derivatives such as, e.g., piroxicam; mucopolysaccharides such as, e.g., thiomucasee; opoid compounds such as, e.g., morphine and morphine-like drugs such as buprenorphine, oxymorphone, hydromorphone, levorphanol, fentanyl and fentany derivatives and analogues; prostaglandins such as, e.g., a member of the PGA, PGB, PGE, or PGF series such as, e.g., misoprostol or enaprostil; a benzamide such as, e.g., metoclopramide, scopolamine; a xanthine such as, e.g., caffeine, theophylline; a catecholamine such as, e.g., ephedrine, salbutamol, terbutaline; a dihydropyridine such as, e.g., nifedipine; a thiazide such as, e.g., hydrochlorotiazide, flunarizine; a sydnonimine such as, e.g., molsidomine; a sulfated polysaccharide such as, e.g., heparin.

EXAMPLE

The following provides an example of the manufacturing process of an embodiment of the composition of the present invention (designated as "GI capsules"). Also described are safety profiles and therapeutic efficacy of the GI capsules.

1. Manufacturing Process of GI Capsules

Figure 6:
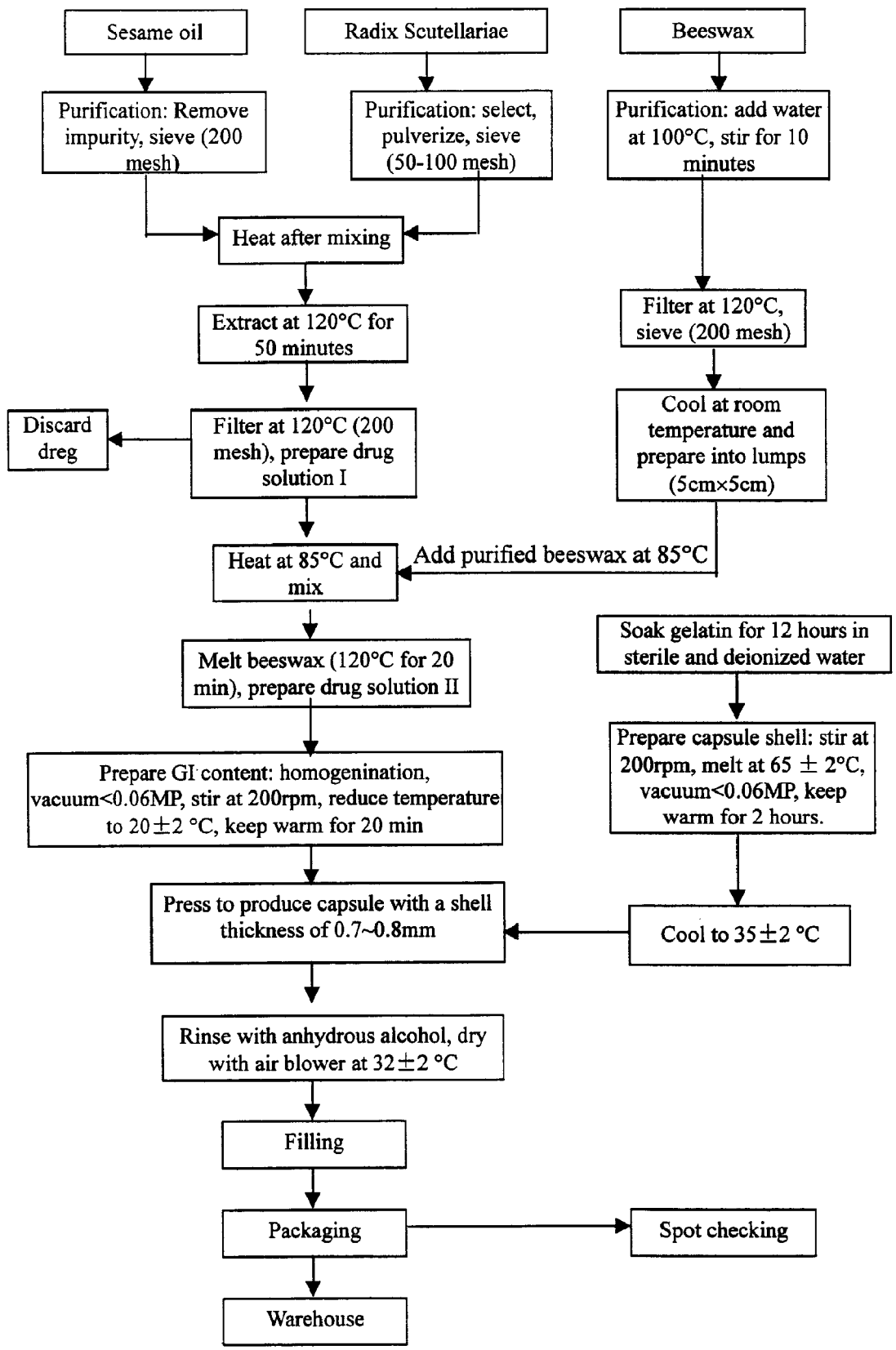
FIG. 6 depicts a manufacturing process for one embodiment of the inventive composition.
Figure 7A:
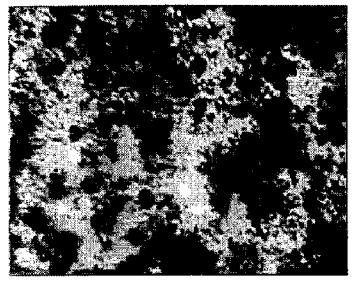
FIGS. 7A-H shows micrographs of the culture of mouse intestinal tissue on day 24, 30, 38, 42, 50, 85, 90, and 97 of culturing, respectively. The left panel is the control group; and the right panel the treatment group.
Figure 7A:
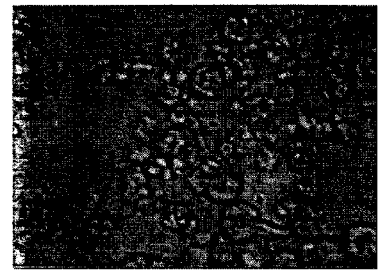
Figure 7B:
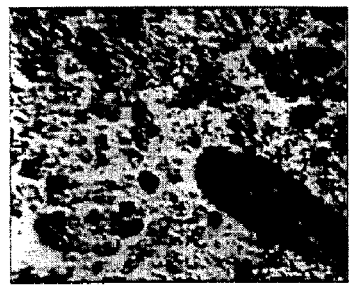
Figure 7B:
Figure 7C:
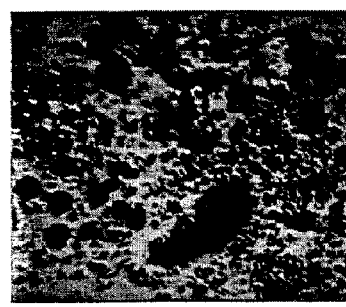
Figure 7C:
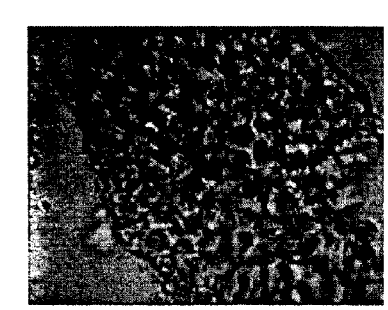
Figure 7D:
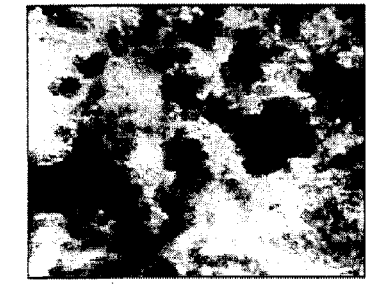
Figure 7D:
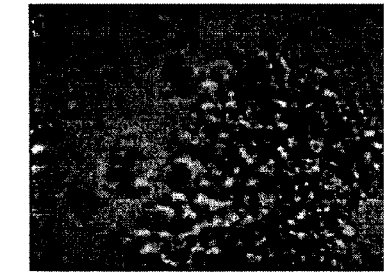
Figure 7E:
Figure 7E:
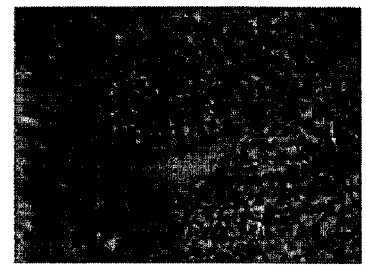
Figure 7F:
Figure 7F:
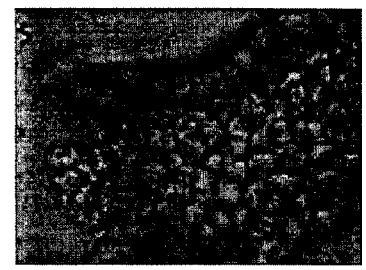
Figure 7G:
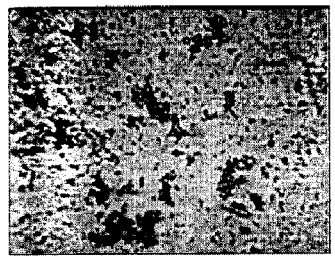
Figure 7G:
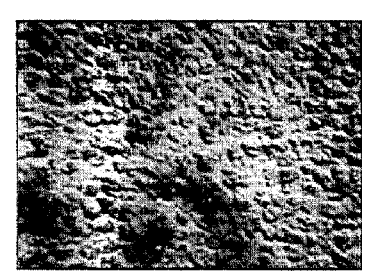
Figure 7H:
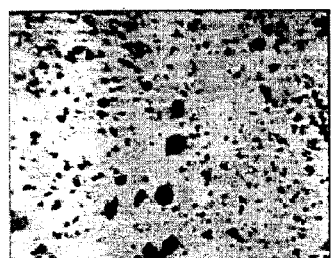
Figure 7H:
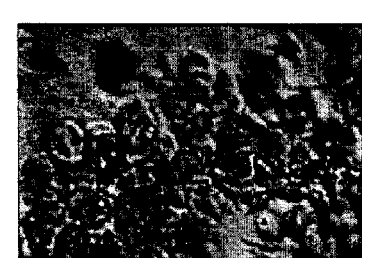
Figure 8A:
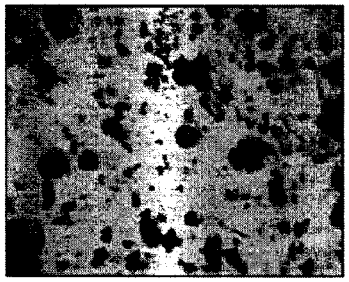
FIGS. 8A-H shows micrographs of the culture of mouse intestinal tissue on day 24, 30, 38, 42, 50, 70, 85, and 90 of culturing, respectively. The left panel is the control group; and the right panel the treatment group.
Figure 8A:
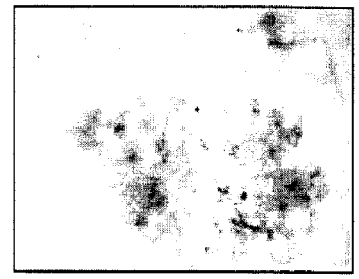
Figure 8B:
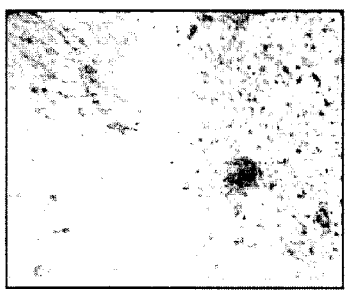
Figure 8B:
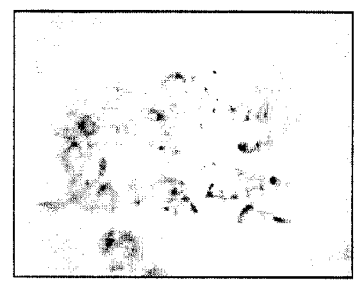
Figure 8C:
Figure 8C:
Figure 8D:
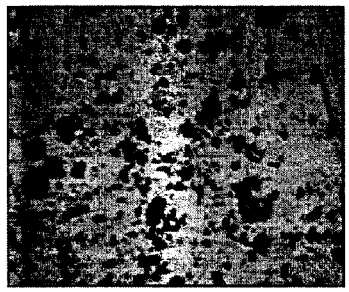
Figure 8D:
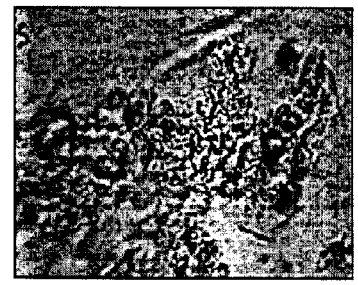
Figure 8E:
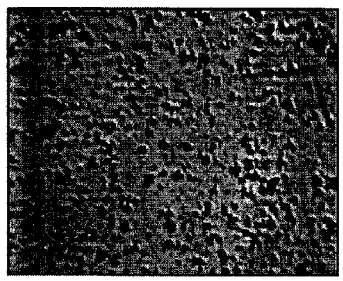
Figure 8E:
Figure 8F:
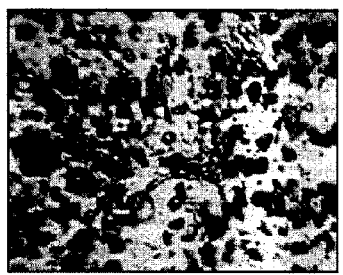
Figure 8F:
Figure 8G:
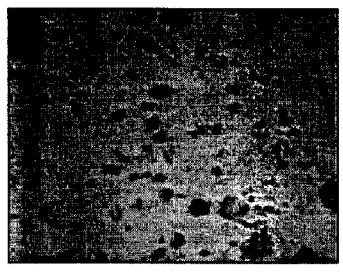
Figure 8G:
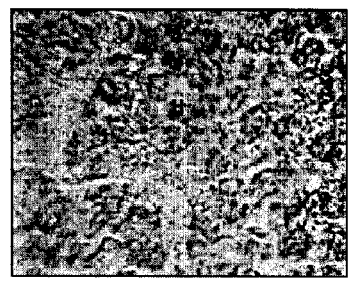
Figure 8H:
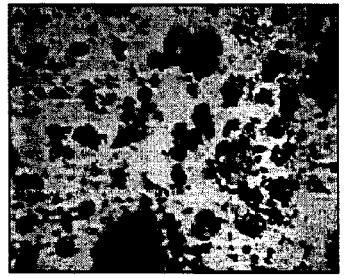
Figure 8H:
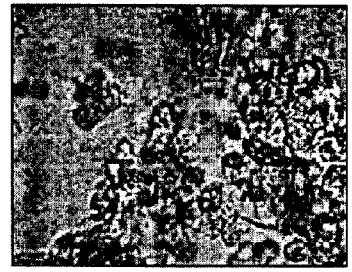

The manufacturing process of the GI capsules is illustrated in a flow chart in FIG. 6. First, raw materials for the production of the GI capsules are purified according to industrial standards. Sesame oil was filtered and transferred to an oil tank. Roots of the plant huangqin (*Radix Scutellariae*) containing flavonoids are washed, cut into small pieces, pulverized, sieved, and transferred into a stock tank. Beeswax was purified by aqueous decoction.

Second, the purified sesame oil and huangqin (100 kg: 5 kg) were added into a reaction tank, stirred and heated at 120° C. for 50 minutes. The dreg was filtered and discarded. The filtrate was labeled as drug oil I.

Third, drug oil I was pumped into another reaction tank, heated and mixed with purified beeswax which was kept warm at 85° C., at a weight ratio of 93 kg:7 kg (drug oil I:beeswax). The mixture was stirred adequately and the heating was stopped once the temperature reached 120° C. The mixture was stirred continuously for 20 minutes, resulting in drug oil II.

Finally, drug oil II was ground in a colloid mill with its gear distance adjusted to 0.6-0.8 μm and output speed at 15 Kg/15 min. Alternatively, drug oil II can be homogenized at 6000-10000 rpm in a homogenizer at 40±2° C. for 15-20 min.

The homogenized mixture was stirred at 100 rpm and vacuumized to below 0.09 MP while the temperature was kept at 40±2° C. for 50 min. When the temperature decreased to about 20° C. and the degree of vacuum reached 0.6~0.8 MP, the homogenized drug oil II was allowed to stand for 20 minutes to obtain the content of the GI capsules.

The content of GI capsules were then filled in soft gel capsules made of gelatin and glycerin according to standard procedures. Briefly, gelatin and preservatives were added to a tank and soaked for 12 hours. With stirring and addition of water, glycerin and preservatives at appropriate proportions the mixture was heated at 65° C. to melt the gelatin. Upon complete melting of the gelatin, the mixture was vacuumized and kept warm for 2 hours with constant stirring, and then cooled to about 32° C. On a soft gel capsule machine the content of GI capsules (e.g., 500 mg/capsule) was filled into a shell made of gelatin and glycerin as described above. The capsule adopts an oval shape and its soft gel shell has a wall thickness of 0.7-0.8 mm.

2. Concentrations of Specific Ingredients in GI Capsules

Concentrations of specific ingredients in GI Capsules, total flavone, β-sitosterol, linoleic acid and oleic acid, were determined using gas chromatography by following procedures described in *Pharmacopoeia of P.R.C*, Edition 2000, Volume 2. Table 1 lists ranges of the concentrations of these ingredients in 100 g of the content of GI Capsules.

TABLE 1

| Ingredient | Content per 100 g |
| --- | --- |
| Natural Vitamin E | 15 mg~50 mg |
| Total Flavone | 20 mg~60 mg |
| β-sitosterol | 0.20 g~1.0 g |
| Linoleic acid | 35 g~55 g |
| Oleic acid | 25 g~45 g |

3. Toxicological Studies of the Content of GI Capsules

1) Acute Toxicity

Content of GI Capsules was administered by oral gavage to Wistar rats (weight: 180-200 g) and Kunming mice (weight: 18-20 g) at various dosages specified in Tables 2 and 3.

Sixteen hours before the administration of the test samples, feeding of the test animals was stopped. During the experiment period, all animals behaved normally with good hair color and brightness and no observable changes were found. The test results are summarized in Tables 2 and 3 for Wistar rats and Kunming mice, respectively. As shown in Tables 2 and 3, oral administration of the content of GI Capsules did not cause any death of the tested animals even at exceedingly high dosages, e.g., 21.5 g/Kg. Thus the content of GI Capsules falls into the non-toxic grade under the standards for grading acute toxicity in animals. Thus, lethal dose for causing death in half of the tested animal ($LD_{50}$) is estimated to be more than 21.5 g/Kg.

TABLE 2

| | Wistar Rate | | | |
|---|---|---|---|---|
| | Male | | Female | |
| Dosage | Animals | Death | Animals | Death |
| 21.5 g/kg | 5 | 0 | 5 | 0 |
| 10.0 g/kg | 5 | 0 | 5 | 0 |
| 4.64 g/kg | 5 | 0 | 5 | 0 |
| 2.15 g/kg | 5 | 0 | 5 | 0 |

TABLE 3

| | Kunming Mice | | | |
|---|---|---|---|---|
| | Male | | Female | |
| Dosage | Animals | Death | Animals | Death |
| 21.5 g/kg | 5 | 0 | 5 | 0 |
| 10.0 g/kg | 5 | 0 | 5 | 0 |
| 4.64 g/kg | 5 | 0 | 5 | 0 |
| 2.15 g/kg | 5 | 0 | 5 | 0 |

2) Micronucleus Tests

Kunming mice with weight of 24~28 g were divided into 5 groups, 10 in each group, 5 female and 5 male. Three dosage groups were given 100, 50, 10 times of 0.083 g/Kg (suggested daily dosage for human intake) of the content of GI Capsules, i.e., 8.3 g/Kg, 4.2 g/Kg and 0.83 g/Kg, respectively. Two control groups, positive control (35 mg/Kg cyclophosphamide (CP)) and negative control (fed with normal food), were also adopted. All test samples were administered to the animals continuously for two days at an interval of 24 hours. Animals were sacrificed by dislocation of cervical vertebra 6 hours after the last administration and their sternal marrow was taken for section, staining and microscopic examination following standard protocols. Each animal was observed for 1000 PCE and quantity of micronucleus PCE was recorded for calculation of micronucleus rates which are summarized in Table 4.

As shown in Table 4, there was no significant difference in micronucleus rates comparing dosage groups to negative control group (P>0.05). In contrast, significant difference was observed between positive control and negative control groups (P<0.01). The group treated with cyclophosphamide, a mutagen known to cause sperm aberration, has a much higher micronucleus rate than that of the negative control group. The test results demonstrate that the content of GI Capsules did not induce the increase of micronucleus rate within the tested dosage ranges.

3) Sperm Aberration Test

Kunming mice with weight of 24~28 g were divided into 5 groups, 10 in each group. Three dosage groups were given 100, 50, 10 times of 0.083 g/Kg (suggested daily dosage for human intake) of the content of GI Capsules, i.e., 8.3 g/Kg, 4.2 g/Kg and 0.83 g/Kg, respectively. Two control groups, positive control (35 mg/Kg cyclophosphamide (CP)) and negative control (fed with normal food), were also adopted. All test samples were administered to the animals continuously for two days at an interval of 24 hours. Animals were sacrificed by dislocation of cervical vertebra 35 days after the initial administration and both epididymides were collected for section, staining and microscopic examination following standard protocols. Each animal was observed for 1000 sperms and quantity of sperms was recorded for calculation of sperm aberration rates which are summarized in Table 5.

TABLE 5

| Group | Number of animals | Quantity of Sperm | Aberrant sperm | Aberration rate (%) |
|---|---|---|---|---|
| 8.30 g/kg | 10 | 10000 | 138 | 1.38 ± 0.13 |
| 4.20 g/kg | 10 | 10000 | 136 | 1.38 ± 0.17 |
| 0.83 g/kg | 10 | 10000 | 132 | 1.32 ± 0.22 |
| CP 35 mg/kg | 10 | 10000 | 2080 | 20.80 ± 0.98 |
| Negative control | 10 | 10000 | 106 | 1.06 ± 0.53 |

As shown in Table 5, there was no significant difference in sperm aberration rates comparing dosage groups to negative control group (P>0.05). In contrast, significant difference was observed between positive control and negative control groups. The group treated with cyclophosphamide has a much higher sperm aberration rate than that of the negative control group. The test results demonstrate that the content of GI Capsules did not cause sperm aberration within the tested dosage ranges.

4) Ames Test

To test mutagenicity of the content of GI Capsules, Ames tests were conducted on four Salmonella strains: TA97a, TA98 frameshift mutation strain, TA100, and TA102 base substitutive mutation strain. Ames (1983) Mutation Research 113:173-215. Five genetic characteristics of these four strains were determined to meet the requirement for the testing. The content of GI Capsules at five concentrations was tested: 5 mg/plate, 2.5 mg/plate, 1.0 mg/plate, 0.5 mg/plate, 0.1 mg/plate. The negative control was PBS. Positive controls

TABLE 4

| Group | Female animals | PCE | Micronucleus PCE | Micronucleus rate (‰) | Male animals | PCE | Micronucleus PCE | Micronucleus rate (‰) |
|---|---|---|---|---|---|---|---|---|
| 8.30 g/kg | 5 | 5000 | 3 | 0.6 ± 0.55 | 5 | 5000 | 3 | 0.6 ± 0.55 |
| 4.20 g/kg | 5 | 5000 | 5 | 1.0 ± 0.71 | 5 | 5000 | 4 | 0.8 ± 0.45 |
| 0.83 g/kg | 5 | 5000 | 5 | 1.0 ± 1.22 | 5 | 5000 | 4 | 0.8 ± 1.10 |
| CP 35 mg/kg | 5 | 5000 | 106 | 21.2 ± 2.28 | 5 | 5000 | 103 | 20.6 ± 2.41 |
| Negative control | 5 | 5000 | 4 | 0.8 ± 0.45 | 5 | 5000 | 3 | 0.6 ± 0.55 | were 2-AF at 100 μg/plate, MMS at 2 μl/plate, fluorenone at 0.2 μg/plate, and 2-AA at 12 μg/plate. Table 6 lists the mutation data of the test samples, positive controls and the negative control.

The test samples were diluted with distilled water into required concentrations and volume of 0.1 ml/10 g BW, and continuously administrated to the mice by oral gavage once a day for 14 days. The mice were fed with normal food during

TABLE 6

| Test substance | TA97a | | TA98 | | TA100 | | TA102 | |
|---|---|---|---|---|---|---|---|---|
| mg/plate | +S9 | −S9 | +S9 | −S9 | +S9 | −S9 | +S9 | −S9 |
| First administration | | | | | | | | |
| GI Capsule | | | | | | | | |
| 5.0 | 136.33 ± 16.50 | 111.33 ± 38.07 | 32.00 ± 8.89 | 26.67 ± 2.52 | 121.00 ± 7.94 | 126.00 ± 19.05 | 319.33 ± 13.32 | 247.33 ± 10.02 |
| 2.5 | 133.67 ± 33.00 | 117.67 ± 11.93 | 25.33 ± 4.93 | 24.33 ± 3.21 | 140.00 ± 17.35 | 147.67 ± 19.09 | 350.67 ± 23.46 | 261.67 ± 67.17 |
| 1.0 | 139.00 ± 14.11 | 129.00 ± 26.46 | 27.33 ± 3.06 | 24.67 ± 3.21 | 139.33 ± 21.20 | 141.00 ± 23.58 | 323.00 ± 26.15 | 265.00 ± 41.62 |
| 0.5 | 112.00 ± 19.97 | 128.67 ± 20.40 | 26.33 ± 2.08 | 25.33 ± 4.51 | 135.67 ± 9.07 | 158.33 ± 18.23 | 349.00 ± 32.91 | 278.33 ± 31.56 |
| 0.1 | 132.00 ± 6.24 | 124.67 ± 6.81 | 28.67 ± 2.52 | 26.00 ± 2.65 | 143.33 ± 6.51 | 139.67 ± 16.56 | 339.00 ± 16.09 | 268.33 ± 18.56 |
| His-(PBS + 0.1 ml DMSO) | | | | | | | | |
| | 117.00 ± 9.42 | 109.50 ± 8.96 | 27.00 ± 4.96 | 24.67 ± 2.89 | 125.25 ± 21.33 | 136.75 ± 23.67 | 351.50 ± 30.92 | 260.75 ± 22.59 |
| Second administration | | | | | | | | |
| GI Capsule | | | | | | | | |
| 5.0 | 135.67 ± 5.13 | 140.00 ± 8.19 | 26.33 ± 3.51 | 27.67 ± 1.53 | 105.33 ± 11.15 | 113.33 ± 17.79 | 317.33 ± 21.13 | 230.67 ± 43.84 |
| 2.5 | 143.67 ± 13.58 | 140.33 ± 10.26 | 31.00 ± 2.65 | 29.33 ± 2.08 | 116.00 ± 11.53 | 125.00 ± 7.21 | 311.00 ± 17.06 | 251.67 ± 18.01 |
| 1.0 | 136.67 ± 13.01 | 130.00 ± 12.12 | 29.33 ± 6.11 | 27.33 ± 2.08 | 121.00 ± 7.55 | 122.33 ± 3.06 | 326.00 ± 18.19 | 243.00 ± 18.11 |
| 0.5 | 151.33 ± 8.08 | 132.00 ± 6.24 | 28.33 ± 5.03 | 28.00 ± 8.61 | 122.67 ± 13.05 | 124.33 ± 7.37 | 331.67 ± 18.56 | 248.00 ± 13.00 |
| 0.1 | 138.67 ± 11.06 | 126.33 ± 4.51 | 30.33 ± 3.06 | 26.67 ± 2.52 | 124.00 ± 5.57 | 117.33 ± 6.66 | 322.33 ± 12.50 | 252.00 ± 10.15 |
| His- (PBS + 0.1 ml DMSO) | | | | | | | | |
| | 141.67 ± 14.57 | 134.33 ± 13.05 | 31.00 ± 3.61 | 29.67 ± 1.53 | 126.33 ± 3.51 | 123.00 ± 4.58 | 320.00 ± 19.16 | 252.67 ± 6.51 |
| Positive Control/plate | | | | | | | | |
| 2-AF 10 ug | 1596.00 ± 33.94 | | 3208.00 ± 362.04 | | | | | |
| Fluorenone 0.2 ug | | 3158.00 ± 398.81 | | 2388.00 ± 220.62 | | | | |
| 2-AF 10 ug | | | | | 1345.00 ± 111.42 | | | |
| MMS 2 ul | | | | | | 1460.00 ± 141.42 | | 2960.00 ± 486.49 |
| 2-AA 12 ug | | | | | | | 1411.00 ± 315.37 | |

As shown in Table 6, under both S9 metabolic and −S9 non-metabolic activation conditions, the content of GI Capsules did not induce mutation in the four strains of *Salmonella* and thus is non-mutagenic within the tested dosage ranges.

4. Laxative Effects of the Content of GI Capsules

The content of GI Capsules was tested for laxative effects, i.e., the effects of the loosening the bowels to relieve constipation, on mouse models for constipation. Healthy Kunming mice were divided randomly into 5 groups, 20 in each group. Three dosage groups were adopted to test the content of GI Capsules: the low dosage of 83.3 mg/kg body weight of the animal (BW) which is the suggested daily dosage for human); the moderate dosage 833 mg/kg BW (10 times of suggested daily dosage); and the high dosage 1666 mg/kg BW (20 times of suggested daily dosage). The negative control group consists of 20 mice fed normally and the positive control group 20 mice fed with diphenoxylate at 50 mg/kg BW.

this period. On the last day of administration, mice were kept on fast for 24 hours overnight, but water was given. Then the content of GI Capsules were administered to mice in the three dosage groups by oral gavage. Twenty minutes later, diphenoxylate (50 mg/kg) was administered to all animals except those in the negative control group at the dosage of 0.1 ml/10 g. Ten minutes later, carbon ink (5% carbo activatus, 10% Arabic gum) was administered to all animals by oral gavage at the dosage of 0. ml/10 g. All animals in each group were divided into two subgroups, 10 mice in each subgroup. One subgroup in each group was kept for observation of their dejection for 24 hours. The other was killed twenty minutes later and cut open the belly to measure the length of small intestine and the distance between pylorus and the front line of carbon ink to calculate carbon moving rates.

Table 7 shows the effects of the treatment on the weight of the mice in the five groups. As shown in Table 7, compared with the negative control group, the content of GI Capsules did not cause any abnormal weight changes in mice within the tested dosage ranges.

TABLE 7

| Group (mg/kg) | Animal No. | 0$^{th}$ day | Weight 7$^{th}$ day | 14$^{th}$ day |
|---|---|---|---|---|
| Negative control group | 20 | 19.6 ± 1.2 | 25.8 ± 0.9 | 29.7 ± 1.3 |
| Low (83.3) | 20 | 19.5 ± 1.2 | 25.9 ± 1.0 | 29.5 ± 1.5 |
| Moderate (833) | 20 | 19.6 ± 1.2 | 25.7 ± 0.9 | 28.6 ± 1.1 |
| High(1666) | 20 | 19.1 ± 1.1 | 25.3 ± 1.2 | 29.1 ± 1.4 |
| Positive control group | 20 | 19.5 ± 1.2 | 25.3 ± 0.9 | 29.2 ± 1.4 |

Table 8 shows the effects of the treatment on dejection of the mice in the five groups. As shown in Table 8, the first dejection times and the total amounts of dejection in the three dosage groups are similar to that in the negative control group. In contrast, the positive control group in which the mice were induced by diphenoxylate to be constipated, had a much longer first dejection time and lower total amount of dejection. These results indicate that the content of GI Capsules has laxative effects on constipated mice.

TABLE 8

| | Animal (No.) | Weight | | |
|---|---|---|---|---|
| Group(mg/kg) | | First dejection time (min) | Dung grain (grain) | Total amounts of dejection (g) |
| Negative control group | 10 | 95.9 ± 34.1* | 36.9 ± 4.6* | 2.8 ± 0.7* |
| Low (83.3) | 10 | 122.8 ± 41.2* | 37.1 ± 6.7* | 2.9 ± 0.6* |
| Moderate (833) | 10 | 99.9 ± 47.2* | 40.5 ± 6.0* | 2.7 ± 0.4* |
| High(1666) | 10 | 106.2 ± 27.0* | 34.0 ± 5.4* | 2.9 ± 0.4* |
| Positive control group | 10 | 230.6 ± 56.0 | 16.4 ± 3.6 | 1.0 ± 0.2 |

*Compare with positive control group p < 0.05

Table 9 shows the moving rates of the bowel content stained with carbon ink in the mice in the five groups. As shown in Table 9, the moving rates in the three dosage groups are similar to that in the negative control group. In contrast, the positive control group had a much lower moving rate. These results confirm that the content of GI Capsules could loosen the bowels to release constipation induced by diphenoxylate, thus having laxative effects on constipated mice.

TABLE 9

| Group (mg/kg) | Animal numbers | Carbon moving rate (%) |
|---|---|---|
| Negative control group | 10 | 65.1 ± 13.0 |
| Low (83.3) | 10 | 62.1 ± 4.5* |
| Moderate (833) | 10 | 60.8 ± 9.7* |
| High (1666) | 10 | 62.1 ± 7.7* |
| Positive control group | 10 | 33.2 ± 10.5 |

*Compare with positive control group P < 0.05

5. Protective Effects of the Content of GI Capsules on Mucosa of Gastrointestinal Tract The content of GI Capsules was tested for its activity in protecting the gastric mucosa of rats from ulcerative effects of anhydrous alcohol. Healthy Wistar male rats with weight of 60-100 g, were divided randomly into 5 groups, 10 in each group. Three dosage groups were adopted to test the content of GI Capsules: the low dosage of 417 mg/kg; the moderate dosage of 834 mg/kg; and the high dosage of 1667 mg/kg, equivalent to 5, 10, and 20 times of the daily dose suggested for administration to human. Negative and positive control groups consisting of 10 rats each were also established.

Rats in the three dosage groups were administered by oral gavage with the content of GI Capsules diluted with distilled water to the desired concentration and volumes (1 ml/100 g weight), one time daily, for continuous 30 days. After the test, all of the experimental animals were kept on fast for 48 hours, but water was given. Afterwards, all animals except those in negative control group were administered with anhydrous alcohol (1 ml per animal) by gavage. On hour later, all animals were sacrificed and dissected. Theirs stomachs were immobilized with 1% formaldehyde and severity of injury on gastric mucosa was observed. Ulcerative indexes were calculated by measuring the length of streak injury if more than 1 mm, scoring 1 for every 1 mm streak, and double scoring if the width is larger than 1 mm. The cumulative scoring is the ulcerative index.

Table 10 lists ulcerative indexes of the rats in the five groups. As shown in Table 10, ulcerative indexes of the rats treated with the content of GI Capsules are much lower than those of the rats in the positive control group. These results indicate that the content of GI Capsules can protect the gastric mucosa from ulcerative effects of alcohol.

TABLE 10

| Group | Number of Animals(n) | Ulcerative Index |
|---|---|---|
| Negative Control | 10 | 3.7 ± 1.6* |
| Low Dosage | 10 | 19.1 ± 6.0* |
| Moderate Dosage | 10 | 18.4 ± 6.6* |
| High Dosage | 10 | 17.4 ± 3.7* |
| Positive Control | 10 | 65.1 ± 20.3 |

*Compare with positive control group P < 0.05

6. Growth of Explants of Intestinal Tissue from Mouse Embryo In Vitro

In this example, in vitro experiments were designed to demonstrate that the inventive composition has unique activities in promoting the growth of cells and tissue in an organ-specific manner. Mucosa of mouse small intestine was harvested from mouse embryos and cultured in vitro. The tissue culture was divided into two groups: the control group cultured in normal tissue culture media (complete MEM) and the treatment group cultured in complete MEM with the addition of the inventive composition.

An embodiment of the inventive composition was used in the in vitro experiment. The composition comprises beeswax at 7% and sitosterol at about 1%, which are homogenized with a sesame oil extract of a combination of dry huangqin (2% w/w), huangbai (2% w/w), huanglian (2% w/w), poppy capsule (2% w/w) and earthworms (2% w/w).

Mucosa of small intestine (about 2 cm) was harvested from embryos of 16-day pregnant Kunming mice immediately after the sacrifice, cut into 1 mm×1 mm pieces, and cultured in MEM in 12-well culture plates (2.5 ml medium/well, 5 mucosa pieces/well) by following a protocol in Donaldson and Kapadia (1980) "Organ culture of gastric mucosa: advantages and limitations" Methods in Cell Biology, Academic Press Inc, 21B:349. About 3 g of the inventive composition was added to the treatment group and 3 ml of MEM was added to the control group. Growth medium in the cultures in both groups was changed every 4-5 days. The cultures were observed for 97 days and microscopic appearance of cultures was recorded.

FIGS. 7A-H show the results of the in vitro experiments on mouse intestinal mucosa culture in the presence and absence of the inventive composition on days 24, 30, 38, 42, 50, 85, 90, and 97, respectively. Pictures of the left column were obtained from the control group and those of the right column from the treatment group. In the first 7 days of culture, mucosa in both control and treatment maintained its integrity. Starting from the 8$^{th}$ day of culture mucosa in both groups began to disintegrate into tiny tissue pieces, almost undetectable with naked eyes. Under microscopic examination, there appeared single cells and clones of cells in both groups. However, starting from the 18$^{th}$ day of culture, cells in the control group gradually darkened, shrunk, and died. See left panels of FIGS. 7A-H.

In contrast, cells in the treatment group maintained strong growth, manifesting typical morphology of viable cells. As shown in the right panel of FIG. 7A, on the 24$^{th}$ day of culture, there were a large number of single intestinal cells growing but no clones. However, on the 30$^{th}$ day of culture, there appeared multiple clones inside which the numbers of cells also increased with the time of culture. See the right panel of FIG. 7B More significantly and surprisingly, by the 38$^{th}$ day, it was observed that a piece of relatively complete intestinal mucosa formed in the culture. The cells in the mucosa adhered to each other in a way resembling that of intestine in vivo. As time went by, the numbers of mucosa pieces increased and scattered through the whole culture. See the right panels of FIGS. 7C-E. At the end of the experiment on the 97$^{th}$ day of culture, a large piece of mucosa was formed by adhesion of the small mucosa pieces to each other. In stuck contrast, all of the cells in the control group died long before, at least within 24 days of culture.

These results demonstrate that the inventive composition is capable of not only promoting growth of mucosal cells of intestine, but also facilitating adhesion of cells to its cognate tissue and formation of mucosa in a culture. The stuck contrast between the control group and the treatment group strongly indicates that the inventive composition has unique activities in stimulation of cell growth and adhesion in a tissue-specific matter. The continuous growth of cells and the formation of mucosal tissue in the culture also suggest that regenerative stem cells might have been activated to produce large numbers of cells to sustain the growth and differentiation of mucosal cells, eventually leading to formation of mucosa in vitro. This is also consistent with the effects on mucosal cells in animal treated with the inventive composition.

7. Growth of Explants of Stomach from Mouse Embryo in Vitro

In this example, in vitro experiments were designed to demonstrate that the inventive composition also has activities promoting the growth of mucosal cells and gastric tissue in an organ-specific manner. Gastric tissue was harvested from mouse embryos and cultured in vitro. The tissue culture is divided into two groups: the control group cultured in normal tissue culture media (complete MEM) and the treatment group cultured in complete MEM with the addition of the inventive composition.

An embodiment of the inventive composition was used in the in vitro experiment. The composition comprises beeswax at 7%, sitosterol at about 1%, obaculactone at about 0.5%, baicalin at about 0.3%, and berberine at about 0.2%, which are mixed in sesame oil.

Gastric tissue of the whole stomach was harvested from embryos of 16-day pregnant Kunming mice immediately after the sacrifice, cut into 1 mm×1 mm pieces, and cultured in MEM in 12-well culture plates (2.5 ml medium/well, 5 tissue pieces/well) by following a protocol in Donaldson and Kapadia (1980) "Organ culture of gastric mucosa: advantages and limitations" Methods in Cell Biology, Academic Press Inc, 21B:349. About 3 g of the inventive composition was added to the treatment group and 3 ml of MEM was added to the control group. Growth medium in the cultures in both groups was changed every 4-5 days. The cultures were observed for 90 days and microscopic appearance of cultures was recorded.

FIGS. 8A-H show the results of the in vitro experiments on mouse intestinal mucosa culture in the presence and absence of the inventive composition on days 24, 30, 38, 42, 50, 70, 85, 90, respectively. Pictures of the left column were obtained from the control group and those of the right column from the treatment group. In the first 7 days of culture, gastric tissue in both control and treatment maintained its integrity. Starting from the 8$^{th}$ day of culture gastric tissue in both groups began to disintegrate into tiny tissue pieces, almost undetectable with naked eyes. Under microscopic examination, there appeared single cells and clones of cells in both groups. However, starting from the 18$^{th}$ day of culture, cells in the control group gradually darkened, shrunk, and died. See left panels of FIGS. 8A-H.

In contrast, cells in the treatment group maintained strong growth, manifesting typical morphology of viable cells. As shown in the right panel of FIG. 8A, on the 24$^{th}$ day of culture, there were clones of gastric cells growing in the culture. The clones continued to grow and the cells inside showed strong vitality. See the right panels of FIGS. 8B-C. By the end of the experiment on the 90$^{th}$ day of culture, the growth of the clones still kept strong with continuous expansion of the gastric tissue in the culture, as shown in FIGS. 8D-H. In contrast, all of the cells in the control group died long before, at least within 24 days of culture.

Consistent with what was observed for intestinal mucosa explants as described above, the inventive composition was also able to promote strong growth of gastric cells and formation of gastric tissue via tissue-specific cell-cell adhesion in vitro. The continuous growth of cells and the formation of gastric tissue in the culture also suggest that regenerative stem cells, presumably epithelial stem cells, might have been activated to produce large numbers of cells to sustain the growth and differentiation of gastric cells, eventually leading to formation of gastric tissue in vitro. This is also consistent with the effects on gastric cells in animals treated with the inventive composition.

What is claimed is:

1. A method for treating a patient having a gastrointestinal cancer, comprising: orally administering to a patient having a gastrointestinal cancer a composition comprising an edible oil homogenized with an edible wax at a concentration ranging from 0.5% to 50% by weight and a sterol compound at a concentration of at least 0.1% by weight, wherein the edible oil, edible wax and sterol compound are homogenized to form colloid with the edible wax adopting a microcrystal form at ambient temperature.

2. The method of claim 1, wherein the gastrointestinal cancer is an upper gastrointestinal cancer selected from the group consisting of esophagus cancer, stomach cancer, pancreas cancer, liver cancer, and cancer of bile ducts.

3. The method of claim 1, wherein the gastrointestinal cancer is a lower gastrointestinal cancer selected from the group consisting of colorectal carcinoma, primary lymphomas, melanoma, and sarcoma of the large bowel.

4. The method of claim 1, wherein the composition contains less than 1% of water by weight.

5. The method of claim 1, wherein the composition is orally administered in an amount of 0.5-15 g per day.

6. The method of claim 1, wherein the composition is orally administered in an amount of 2-8 g per day.

7. The method of claim 1, wherein the composition is formulated in 0.1-0.5 g soft gel capsules, 1-10 of which are orally administered to the host twice a day.

8. The method of claim 1, wherein the sterol compound is a combination of stigmasterol, β-sitosterol, and campesterol.

9. The method of claim 1, wherein the sterol compound is β-sitosterol.

10. The method of claim 1, wherein the edible wax is selected from the group consisting of beeswax, castorwax, glycowax, and carnaubawax.

11. The method of claim 1, wherein the edible oil is selected from the group consisting of corn oil, wheat germ oil, soy bean oil, rice bran oil, rapeseed oil, sesame oil, and fish oil.

12. The method of claim 1, wherein the edible oil is sesame oil.

13. The method of claim 1, wherein the concentration of the sterol compound is 0.5% to 20% by weight.

14. The method of claim 1, wherein the concentration of the sterol compound is 1% to 10% by weight.

15. The method of claim 1, wherein the concentration of the edible wax is 3% to 30% by weight.

16. The method of claim 1, wherein the composition is formulated in a soft or hard gel capsule.

17. The method of claim 1, wherein the composition further comprises baicalin.

18. The method of claim 1, wherein the composition further comprises an extract of huangqin.

19. The method of claim 1, wherein the composition further comprises an extract of a combination of huangqin, huangbai and huanglian.

20. The method of claim 1, wherein the sterol compound is selected from the group consisting of stigmasterol, campesterol, β-sitosterol, chalinosterol, clionasterol, brassicasterol, α-spinasterol, daucosterol, desmosterol, and poriferasterol, at a concentration of at least 0.1% by weight based on the total weight of the composition.

21. The method of claim 1, wherein the microcrystal form of beeswax is 0.1-100 μm in length.

22. The method of claim 1, wherein the microcrystals of beeswax are dispersed substantially uniformly in the edible oil.

* * * * *